(12) United States Patent
Dehmlow et al.

(10) Patent No.: US 8,039,493 B2
(45) Date of Patent: Oct. 18, 2011

(54) BIARYL SULFONAMIDE DERIVATIVES

(75) Inventors: Henrietta Dehmlow, Loerrach (DE); Ulrike Obst Sander, Reinach (CH); Tanja Schulz-Gasch, Liestal (CH); Matthew Wright, Basel (CH)

(73) Assignee: Hoffmann-La Roche Inc., Nutley, NJ (US)

( * ) Notice: Subject to any disclaimer, the term of this patent is extended or adjusted under 35 U.S.C. 154(b) by 607 days.

(21) Appl. No.: 12/211,835

(22) Filed: Sep. 17, 2008

(65) Prior Publication Data

US 2009/0088459 A1    Apr. 2, 2009

(51) Int. Cl.
| | | |
|---|---|---|
| *A61K 31/38* | (2006.01) | |
| *A61K 31/18* | (2006.01) | |
| *C07C 311/16* | (2006.01) | |
| *C07D 333/22* | (2006.01) | |

(52) U.S. Cl. ........ 514/357; 514/438; 514/604; 514/605; 549/75; 546/334; 564/91; 564/92; 564/99

(58) Field of Classification Search ............ 549/75; 564/91, 92, 99; 546/334; 514/357, 438, 514/604, 605
See application file for complete search history.

(56) References Cited

FOREIGN PATENT DOCUMENTS
| | | |
|---|---|---|
| WO | WO 00/54759 | 9/2000 |
| WO | WO 03/099769 | 12/2003 |
| WO | WO 03/099775 | 12/2003 |

OTHER PUBLICATIONS

Anderson et al, *Molecular Pharmacology*, 66:6 (2004) 1440-1452 XP009115071.
Panday et al, *Bioorganic & Medicinal Chemistry Letters*, 16:19 5231-5237 (2006).
Lund et al., Arterioscler. Thomb. Vasc. Biol., 23, pp. 1169-1177 (2003).
Mitro et al., Nature, 445, pp. 219-223 (2007).
Joseph et al., Curr. Opin. Pharmacol, 3, pp. 192-197 (2003).
Cao et al., J. Biol. Chem., 278, pp. 1131-1136 (2003).

*Primary Examiner* — Bernard Dentz
(74) *Attorney, Agent, or Firm* — George W. Johnston; Dennis P. Tramaloni; Brian C. Remy

(57) ABSTRACT

The invention is concerned with novel biaryl sulfonamide derivatives of formula (I)

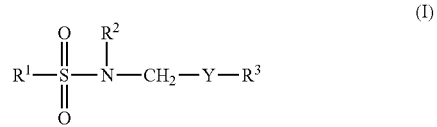

wherein $R^1$ to $R^3$ and Y are as defined in the description and in the claims, as well as physiologically acceptable salts and esters thereof. These compounds bind to LXR alpha and LXR beta and can be used as medicaments.

23 Claims, No Drawings

BIARYL SULFONAMIDE DERIVATIVES

PRIORITY TO RELATED APPLICATION(S)

This application claims the benefit of European Patent Application No. 07117437.9, filed Sep. 27, 2007. The entire contents of the above-identified applications are hereby incorporated by reference.

FIELD OF THE INVENTION

The present invention is directed to, for example, novel biaryl sulfonamide derivatives, their manufacture and their use as medicaments. In particular, the present invention provides the novel compound of formula (I), which bind to LXRalpha and/or LXRbeta, and pharmaceutically acceptable compositions thereof.

BACKGROUND OF THE INVENTION

Liver-X-Receptors (LXRs) are members of the nuclear hormone receptor superfamily. The LXRs are activated by endogenous oxysterols and glucose and regulate the transcription of genes controlling multiple metabolic pathways. Two subtypes, LXRalpha and LXRbeta, have been described (Willy, P. J. et al., Genes Dev. 1995, 9:1033-45; Song, C. et al., Proc Natl Acad Sci USA. 1994, 91:10809-13). LXRbeta is ubiquitously expressed, while LXRalpha is predominantly expressed in cholesterol metabolizing tissues such as the liver, adipose, intestine and macrophage. The LXRs modulate a variety of physiological responses including regulation of cholesterol absorption, cholesterol elimination (bile acid synthesis), and transport of cholesterol from peripheral tissues via plasma lipoproteins to the liver. The LXRs also appear to regulate genes involved in glucose metabolism, cholesterol metabolism in the brain, cellular differentiation and apoptosis, inflammation, and infectious diseases (Geyeregger, R. et al., Cell. Mol. Life. Sci. 2006, 63:524-539).

About half of all patients with coronary artery disease have low concentrations of plasma high-density lipoprotein cholesterol (HDL-C). The atheroprotective function of HDL was first highlighted almost 25 years ago and stimulated exploration of the genetic and environmental factors that influence HDL-C levels (Miller N E., Lipids 1978, 13:914-9). The protective function of HDL derives from its role in a process termed reverse cholesterol transport (Forrester, J. S. and Shah, P. K., Am. J. Cardiol. 2006, 98:1542-49). HDL mediates the removal of cholesterol from cells in peripheral tissues, including macrophage foam cells in the atherosclerotic lesions of the arterial wall. HDL delivers its cholesterol to the liver and sterol-metabolizing organs for conversion to bile and elimination in feces. Studies have shown that HDL-C levels are predictive of coronary artery disease risk independently of low-density lipoprotein cholesterol (LDL-C) levels (Gordon, T. et al., Am J Med. 1977, 62:707-14).

At present, the estimated age-adjusted prevalence among Americans age 20 and older who have HDL-C of less than 35 mg/dl is 16% (males) and 5.7% (females). A substantial increase of HDL-C is currently achieved by treatment with niacin in various formulations. However, the substantial unfavorable side-effects limit the therapeutic potential of this approach.

It has been observed that as many as 90% of the 14 million diagnosed type 2 diabetic patients in the United States are overweight or obese, and a high proportion of type 2 diabetic patients have abnormal concentrations of lipoproteins. Studies have shown that the prevalence of total cholesterol>240 mg/dl is 37% in diabetic men and 44% in women. The rates for LDL-C>160 mg/dl are 31% and 44%, and for HDL-C<35 mg/dl are 28% and 11%, in diabetic men and women respectively. Diabetes is a disease in which a patient's ability to control glucose levels in blood is decreased because of partial impairment in response to the action of insulin. Type II diabetes (T2D) is also called non-insulin dependent diabetes mellitus (NIDDM) and has been shown to afflict 80-90% of all diabetic patients in developed countries. In T2D, the pancreatic Islets of Langerhans continue to produce insulin. However, the target organs for insulin action, mainly muscle, liver and adipose tissue, exhibit a profound resistance to insulin stimulation. The body continues to compensate by producing unphysiologically high levels of insulin, which ultimately decreases in the later stages of the disease, due to exhaustion and failure of pancreatic insulin-producing capacity. Thus, T2D is a cardiovascular-metabolic syndrome associated with multiple co-morbidities, including insulin resistance, dyslipidemia, hypertension, endothelial dysfunction and inflammatory atherosclerosis.

The first line of treatment for dyslipidemia and diabetes at present generally involves a low-fat and low-glucose diet, exercise and weight loss. However, compliance can be moderate, and as the disease progresses, treatment of the various metabolic deficiencies becomes necessary with lipid-modulating agents such as statins and fibrates for dyslipidemia, and hypoglycemic drugs, e.g. sulfonylureas, metformin, or insulin sensitizers of the thiazolidinedione (TZD) class of PPARγ-agonists, for insulin resistance. Recent studies provide evidence that modulators of LXRs would result in compounds with enhanced therapeutic potential, and as such, modulators of LXRs should improve the plasma lipid profile, and raise HDL-C levels (Lund, E. G. et al., Arterioscler. Thromb. Vasc. Biol. 2003, 23:1169-77; Mitro, N. et al., Nature 2007, 445: 219-23). LXRs are also known to control the efflux of cholesterol from the macrophage foam cell of the atherosclerotic lesion, and agonists of LXRs have been shown to be atheroprotective (Joseph, S. B. and Tontonoz, P., Curr. Opin. Pharmacol. 2003, 3:192-7). Thus, modulators of LXRs would be effective treatments for the atherosclerotic disease which underlies the cardiovascular morbidity and mortality of stroke and heart disease. Recent observations also suggest that there is an independent LXR mediated effect on insulin-sensitization in addition to its role in atheroprotection (Cao, G. et al., J Biol Chem. 2003, 278:1131-6). Thus LXR modulators can also show superior therapeutic efficacy on HDL-raising and atheroprotection, with additional effects on diabetes, compared to current therapies.

While compounds that bind to and activate LXR alpha and LXR beta have previously been suggested (e.g.: WO 03/099769), the present invention provides the novel compounds of formula (I) which bind to LXR alpha and/or LXR beta and unexpectedly exhibit improved pharmacological properties compared to the compounds known in the art, concerning e.g. metabolic stability, selectivity, bioavailability and activity.

SUMMARY OF THE INVENTION

The invention is concerned with novel biaryl sulfonamide derivatives of the formula (I)

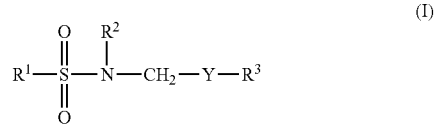

wherein
Y is arylene or heteroarylene, which arylene or heteroarylene can optionally be substituted with 1 to 4 substituents independently selected from the group consisting of halogen, lower-alkyl, lower-alkoxy, fluoro-lower-alkyl and fluoro-lower-alkoxy;

$R^1$ is lower-alkyl, fluoro-lower-alkyl, aryl, aryl-lower-alkyl, heteroaryl, heteroaryl-lower-alkyl, cycloalkyl or cycloalkyl-lower-alkyl, wherein an aryl, heteroaryl or cycloalkyl can optionally be substituted with 1 to 4 substituents independently selected from the group consisting of halogen, CN, lower-alkyl, lower-alkoxy, fluoro-lower-alkyl, fluoro-lower-alkoxy, lower-alkoxy-carbonyl and phenyl;

$R^2$ is lower-alkyl, lower-alkoxy-lower-alkyl, lower-alkoxy-carbonyl-lower-alkyl, amino-carbonyl-lower-alkyl, cycloalkyl, cycloalkyl-lower-alkyl, aryl-lower-alkyl, aryl-C(O), heteroaryl-lower-alkyl, heteroaryl-C(O) or heterocyclyl-lower-alkyl, wherein a cycloalkyl, aryl, heteroaryl or heterocyclyl can optionally be substituted with 1 to 4 substituents independently selected from the group consisting of halogen, lower-alkyl, CN, fluoro-lower-alkyl, lower-alkoxy, fluoro-lower-alkoxy and lower-alkoxy-carbonyl;

$R^3$ is aryl or heteroaryl, which aryl or heteroaryl is substituted with $R^4SO_2$—, $N(R^5R^6)SO_2$—, $R^4SO_2NR^7$— or $N(R^5R^6)SO_2NR^7$—, and which aryl or heteroaryl can optionally be substituted with 1 to 3 additional substituents independently selected from the group consisting of hydroxy-lower-alkyl, halogen, CN, lower-alkyl, fluoro-lower-alkyl, lower-alkoxy, fluoro-lower-alkoxy and lower-alkoxy-carbonyl;

$R^4$ is lower-alkyl;

$R^5$, $R^6$ and $R^7$ independently from each other are hydrogen or lower-alkyl;

and pharmaceutically acceptable salts and esters thereof;

with the proviso that the compound is not N-[[3'-[(methylsulfonyl)amino][1,1'-biphenyl]-3-yl]methyl]-N-(3-pyridinylmethyl)-ethanesulfonamide.

Further, the invention is concerned with a process for the manufacture of the above compounds, pharmaceutical preparations which contain such compounds as well as the use of these compounds for the production of pharmaceutical preparations.

DETAILED DESCRIPTION OF THE INVENTION

The novel compounds of the present invention have been found to bind to and selectively activate LXR alpha and/or LXR beta or coactivate LXR alpha and LXR beta. Consequently, cholesterol absorption is reduced, HDL cholesterol is increased, and inflammatory atherosclerosis is reduced. Since multiple facets of combined dyslipidemia and cholesterol homeostasis are addressed by LXR modulators, novel compounds of the present invention have an enhanced therapeutic potential compared to the compounds already known in the art.

A. Definitions

Unless otherwise indicated, the following definitions are set forth to illustrate and define the meaning and scope of the various terms used to describe the invention herein. In this specification the term "lower" is used to mean a group consisting of one to seven, preferably of one to four carbon atom(s).

The term "halogen" refers to fluorine, chlorine, bromine and iodine, with fluorine, chlorine and bromine being preferred.

The term "alkyl", alone or in combination with other groups, refers to a branched or straight-chain monovalent saturated aliphatic hydrocarbon radical of one to twenty carbon atoms, preferably one to sixteen carbon atoms, more preferably one to ten carbon atoms. Lower-alkyl groups as described below also are preferred alkyl groups.

The term "lower-alkyl", alone or in combination with other groups, refers to a branched or straight-chain monovalent alkyl radical of one to seven carbon atoms, preferably one to four carbon atoms. This term is further exemplified by such radicals as methyl, ethyl, n-propyl, isopropyl, n-butyl, s-butyl, t-butyl and the like.

Lower-alkyl groups can optionally be substituted, e.g. by hydroxy. Such groups are referred to as "hydroxy-lower-alkyl". Examples of hydroxy-lower-alkyl groups are e.g. hydroxymethyl, hydroxyethyl, hydroxypropyl or hydroxybutyl groups, preferably hydroxyethyl.

The term "fluoro-lower-alkyl" refers to lower-alkyl groups which are mono- or multiply substituted with fluorine. Examples of fluoro-lower-alkyl groups are e.g. $CFH_2$, $CF_2H$, $CF_3$, $CF_3CH_2$, $CF_3(CH_2)_2$, $(CF_3)_2CH$ and $CF_2H$—$CF_2$.

The term "amino", alone or in combination, signifies a primary, secondary or tertiary amino group bonded via the nitrogen atom, with the secondary amino group carrying an alkyl or cycloalkyl substituent and the tertiary amino group carrying two similar or different alkyl or cycloalkyl substituents or the two nitrogen substitutents together forming a ring, such as, for example, —$NH_2$, methylamino, ethylamino, dimethylamino, diethylamino, methyl-ethylamino, pyrrolidin-1-yl or piperidino etc.

The term "cycloalkyl" refers to a monovalent carbocyclic radical of 3 to 10 carbon atoms, preferably 3 to 6 carbon atoms, such as cyclopropyl, cyclobutyl, cyclopentyl, or cyclohexyl. Cycloalkyl groups can optionally be substituted as described below in the description and claims.

The term "alkoxy" refers to the group R'—O—, wherein R' is an alkyl. The term "lower-alkoxy" refers to the group R'—O—, wherein R' is a lower-alkyl.

The term "fluoro-lower-alkoxy" refers to the group R"—O—, wherein R" is fluoro-lower-alkyl. Examples of fluoro-lower-alkoxy groups are e.g. $CFH_2$—O, $CF_2H$—O, $CF_3$—O, $CF_3CH_2$—O, $CF_3(CH_2)_2$—O, $(CF_3)_2CH$—O, and $CF_2H$—$CF_2$—O.

The term "alkylene" refers to a straight chain or branched divalent saturated aliphatic hydrocarbon group of 1 to 20 carbon atoms, preferably 1 to 16 carbon atoms, more preferably up to 10 carbon atoms. Lower-alkylene groups as described below also are preferred alkylene groups.

The term "lower-alkylene" refers to a straight chain or branched divalent saturated aliphatic hydrocarbon group of 1 to 7, preferably 1 to 6 or 3 to 6 carbon atoms. Straight chain alkylene or lower-alkylene groups are preferred.

The term "aryl", alone or in combination, relates to the phenyl or naphthyl group, preferably the phenyl group, which can optionally be substituted by 1 to 5, preferably 1 to 3, substituents independently selected from the group consisting of lower-alkyl, lower-alkoxy, halogen, hydroxy, CN, $CF_3$, amino, aminocarbonyl, carboxy, $NO_2$, dioxo-lower-alkylene (forming e.g. a benzodioxyl group), lower-alkylsufonyl, aminosulfonyl, lower-alkylcarbonyl, lower-alkylcarbonyloxy, lower-alkylcarbonyl-NH, lower-alkoxycarbonyl, fluoro-lower-alkyl, fluoro-lower-alkoxy, lower-alkoxy-lower-alkyl, cycloalkyl and phenyloxy. Unless stated otherwise, preferred substituents are halogen, lower-alkyl, fluoro-lower-alkyl, CN and lower-alkoxycarbonyl. Furthermore, aryl groups can preferably be substituted as described below in the description and claims.

The term "heterocyclyl", alone or in combination, signifies a saturated or partially unsaturated 4- to 10-membered, mono- or bicyclic heterocycle which contains one or more hetero atoms, preferably one to three, selected from nitrogen, oxygen and sulphur. Examples of such heterocyclyl groups are piperidinyl, piperazinyl, pyrrolidinyl, imidazolidinyl, pyrazolidinyl, pyranyl, [1,3]dioxolanyl, tetrahydrofuranyl, morpholinyl and oxetanyl. Preferred heterocyclyl are [1,3]

dioxolanyl, pyrrolidinyl and tetrahydrofuranyl. A heterocyclyl group may optionally have a substitution pattern as described earlier in connection with the term "aryl". Furthermore, heterocyclyl groups can preferably be substituted as described below in the description and claims.

The term "heteroaryl" refers to an aromatic 5 to 6 membered monocyclic ring or 9 to 10 membered bicyclic ring which can comprise 1, 2 or 3 atoms selected from nitrogen, oxygen and/or sulphur, such as furanyl, pyridinyl, pyridazinyl, pyrimidinyl, pyrazinyl, thiophenyl, isoxazolyl, oxazolyl, oxadiazolyl, imidazolyl, pyrrolyl, pyrazolyl, triazolyl, tetrazolyl, thiazolyl, isothiazolyl, 1,2,3-thiadiazolyl, benzoimidazolyl, indolyl, indazolyl, benzoisothiazolyl, benzoxazolyl, benzoisoxazolyl, 3-thieno[3,2-c]pyridin-4-yl and quinolinyl. Preferred heteroaryl groups are isoxazolyl, oxadiazolyl, thiazolyl, furanyl, thiophenyl and pyridinyl. A heteroaryl group may optionally have a substitution pattern as described earlier in connection with the term "aryl". Furthermore, heteroaryl groups can preferably be substituted as described below in the description and claims.

The term "arylene" refers to a divalent aryl as defined above. The term "heteroarylene" refers to a divalent heteroaryl as defined above.

Compounds of formula (I) may form pharmaceutically acceptable acid addition salts. Examples of such pharmaceutically acceptable salts are salts of compounds of formula (I) with physiologically compatible mineral acids, such as hydrochloric acid, sulphuric acid, sulphurous acid or phosphoric acid; or with organic acids, such as methanesulphonic acid, p-toluenesulphonic acid, acetic acid, lactic acid, trifluoroacetic acid, citric acid, fumaric acid, maleic acid, tartaric acid, succinic acid or salicylic acid. The term "pharmaceutically acceptable salts" refers to such salts. Compounds of formula (I) may further form salts with bases. Examples of such salts are alkaline, earth-alkaline and ammonium salts such as e.g. Na—, K—, Ca— and trimethylammoniumsalt. The term "pharmaceutically acceptable salts" also refers to such salts.

The term "pharmaceutically acceptable esters" embraces compounds of formula (I) in which hydroxy groups have been converted to the corresponding esters with inorganic or organic acids such as, nitric acid, sulphuric acid, phosphoric acid, citric acid, formic acid, maleic acid, acetic acid, succinic acid, tartaric acid, methanesulphonic acid, p-toluenesulphonic acid and the like, which are non toxic to living organisms.

All references cited herein are hereby incorporated by reference in their entirety.

B. Detailed Description of the Invention

In detail, the present invention relates to compounds of formula (I)

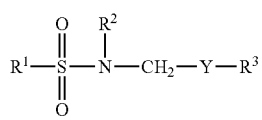

wherein

Y is arylene or heteroarylene, which arylene or heteroarylene can optionally be substituted with 1 to 4 substituents independently selected from the group consisting of halogen, lower-alkyl, lower-alkoxy, fluoro-lower-alkyl and fluoro-lower-alkoxy;

$R^1$ is lower-alkyl, fluoro-lower-alkyl, aryl, aryl-lower-alkyl, heteroaryl, heteroaryl-lower-alkyl, cycloalkyl or cycloalkyl-lower-alkyl, wherein an aryl, heteroaryl or cycloalkyl can optionally be substituted with 1 to 4 substituents independently selected from the group consisting of halogen, CN, lower-alkyl, lower-alkoxy, fluoro-lower-alkyl, fluoro-lower-alkoxy, lower-alkoxy-carbonyl and phenyl;

$R^2$ is lower-alkyl, lower-alkoxy-lower-alkyl, lower-alkoxy-carbonyl-lower-alkyl, amino-carbonyl-lower-alkyl, cycloalkyl, cycloalkyl-lower-alkyl, aryl-lower-alkyl, aryl-C(O), heteroaryl-lower-alkyl, heteroaryl-C(O) or heterocyclyl-lower-alkyl, wherein a cycloalkyl, aryl, heteroaryl or heterocyclyl can optionally be substituted with 1 to 4 substituents independently selected from the group consisting of halogen, lower-alkyl, CN, fluoro-lower-alkyl, lower-alkoxy, fluoro-lower-alkoxy and lower-alkoxy-carbonyl;

$R^3$ is aryl or heteroaryl, which aryl or heteroaryl is substituted with $R^4SO_2$—, $N(R^5R^6)SO_2$—, $R^4SO_2NR^7$— or $N(R^5R^6)SO_2NR^7$—, and which aryl or heteroaryl can optionally be substituted with 1 to 3 additional substituents independently selected from the group consisting of hydroxy-lower-alkyl, halogen, CN, lower-alkyl, fluoro-lower-alkyl, lower-alkoxy, fluoro-lower-alkoxy and lower-alkoxy-carbonyl;

$R^4$ is lower-alkyl;

$R^5$, $R^6$ and $R^7$ independently from each other are hydrogen or lower-alkyl;

and pharmaceutically acceptable salts and esters thereof;

with the proviso that the compound is not N-[[3'-[(methylsulfonyl)amino][1,1'-biphenyl]-3-yl]methyl]-N-(3-pyridinylmethyl)-ethanesulfonamide.

Compounds of formula (I) are individually preferred, pharmaceutically acceptable salts thereof are individually preferred and pharmaceutically acceptable esters thereof are individually preferred, with the compounds of formula (I) being particularly preferred.

The compounds of formula (I) can have one or more asymmetric C atoms and can therefore exist as an enantiomeric mixture, mixture of stereoisomers or as optically pure compounds.

Preferred compounds of the present invention are those, wherein Y is phenylene or a heteroarylene selected from the group consisting of thiophenylene, oxadiazolylene, thiazolylene, furanylene and pyridinylene, which phenylene or heteroarylene is optionally substituted with 1 to 2 halogen, more preferably substituted with 1 halogen. More preferably, Y is phenylene, thiophenylene or pyridinylene, which phenylene is optionally substituted with halogen. Even more preferably, Y is

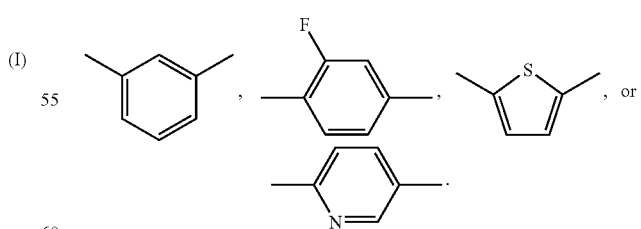

Other preferred compounds of the present invention are those, wherein $R^1$ is lower-alkyl, fluoro-lower-alkyl, aryl, aryl-lower-alkyl, heteroaryl or cycloalkyl-lower-alkyl, wherein an aryl, heteroaryl or cycloalkyl can optionally be substituted with 1 to 3 substituents, preferably with 1 to 2 substituents, independently selected from the group consisting of halogen, CN, lower-alkyl, lower-alkoxy, fluoro-lower-alkyl and lower-alkoxy-carbonyl. Thiophenyl is a preferred heteroaryl, in context with $R^1$. More preferably, $R^1$ is lower-alkyl, fluoro-lower-alkyl or phenyl, which phenyl is optionally substituted with halogen, CN or fluoro-lower-alkyl. Even more preferably, $R^1$ is isopropyl, trifluoromethyl, 2-chloro-phenyl, 2-fluoro-phenyl, 2-cyano-phenyl or 2-trifluoromethyl-phenyl.

Another preferred embodiment of the present invention relates to compounds of formula (I) as described above, wherein $R^2$ is lower-alkyl, lower-alkoxy-lower-alkyl, lower-alkoxy-carbonyl-lower-alkyl, amino-carbonyl-lower-alkyl, cycloalkyl-lower-alkyl, aryl-lower-alkyl, aryl-C(O), heteroaryl-lower-alkyl or heterocyclyl-lower-alkyl, wherein a cycloalkyl, aryl, heteroaryl or heterocyclyl can optionally be substituted with 1 to 3 substituents, preferably with 1 to 2 substituents, independently selected from the group consisting of halogen and lower-alkyl. Isoxazolyl is a preferred heteroaryl in context with $R^2$. [1,3]Dioxolanyl, pyrrolidinyl and tetrahydrofuranyl are preferred heterocyclyl in context with $R^2$. Preferably, $R^2$ is lower-alkyl, cycloalkyl-lower-alkyl or aryl-lower-alkyl, wherein aryl-lower-alkyl can optionally be substituted with halogen. More preferably, $R^2$ is isopropyl, isobutyl, cyclopropylmethyl or 2-fluoro-benzyl.

Furthermore, it is preferred, that $R^3$ is aryl or heteroaryl, which aryl or heteroaryl is substituted with $R^4SO_2$—, $N(R^5R^6)SO_2$— or $R^4SO_2NR^7$—, and which aryl or heteroaryl can optionally be substituted with 1 to 2 additional substituents independently selected from hydroxy-lower-alkyl, preferably with 1 hydroxy-lower-alkyl, wherein $R^4$, $R^5$, $R^6$ and $R^7$ are as defined above. Pyridinyl is a preferred heteroaryl in context with $R^3$. More preferably, $R^3$ is phenyl which is substituted with $R^4SO_2$—, wherein $R^4$ is as defined above. Even more preferably, $R^3$ is 3-methansulfonyl-phenyl.

Furthermore, it is preferred that $R^4$ is methyl. It is also preferred that $R^5$ is hydrogen. Preferably, $R^6$, is hydrogen or tert-butyl. It is also preferred that $R^7$ is hydrogen.

In particular, preferred compounds are the compounds of formula (I) described in the examples as individual compounds as well as pharmaceutically acceptable salts and esters thereof.

Preferred compounds of formula (I) are those selected from the group consisting of N-Benzyl-N-[5-(3-methanesulfonyl-phenyl)-thiophen-2-ylmethyl]-2-trifluoromethyl-benzenesulfonamide,
N-Benzyl-N-[5-(3-methanesulfonylamino-phenyl)-thiophen-2-ylmethyl]-2-trifluoromethyl-benzenesulfonamide,
N-Benzyl-N-[5-(3-methanesulfonyl-phenyl)-[1,3,4]oxadiazol-2-ylmethyl]-2-trifluoromethyl-benzenesulfonamide,
N-Benzyl-2-chloro-N-[5-(3-methanesulfonyl-phenyl)-thiophen-2-ylmethyl]-benzenesulfonamide,
2-Chloro-N-isobutyl-N-[5-(3-methanesulfonyl-phenyl)-thiophen-2-ylmethyl]-benzenesulfonamide,
N-Benzoyl-2-chloro-N-[5-(3-methanesulfonyl-phenyl)-thiophen-2-ylmethyl]-benzenesulfonamide,
N-Benzyl-3-chloro-N-[5-(3-methanesulfonyl-phenyl)-thiophen-2-ylmethyl]-benzenesulfonamide,
3-Chloro-N-isobutyl-N-[5-(3-methanesulfonyl-phenyl)-thiophen-2-ylmethyl]-benzenesulfonamide,
N-Benzoyl-3-chloro-N-[5-(3-methanesulfonyl-phenyl)-thiophen-2-ylmethyl]-benzenesulfonamide,
N-Benzyl-2-chloro-N-[2-(3-methanesulfonyl-phenyl)-thiazol-5-ylmethyl]-benzenesulfonamide,
2-Chloro-N-isobutyl-N-[2-(3-methanesulfonyl-phenyl)-thiazol-5-ylmethyl]-benzenesulfonamide,
N-Benzoyl-2-chloro-N-[2-(3-methanesulfonyl-phenyl)-thiazol-5-ylmethyl]-benzenesulfonamide,
2-Chloro-N-isobutyl-N-[5-(3-methanesulfonyl-phenyl)-furan-2-ylmethyl]-benzenesulfonamide,
2-Chloro-N-isobutyl-N-[4-(3-methanesulfonyl-phenyl)-thiophen-2-ylmethyl]-benzenesulfonamide,
N-Isobutyl-N-[5-(3-methanesulfonyl-phenyl)-thiophen-2-ylmethyl]-methanesulfonamide,
Ethanesulfonic acid isobutyl-[5-(3-methanesulfonyl-phenyl)-thiophen-2-ylmethyl]-amide,
2-Fluoro-N-isobutyl-N-[5-(3-methanesulfonyl-phenyl)-thiophen-2-ylmethyl]-benzenesulfonamide,
2,6-Dichloro-N-isobutyl-N-[5-(3-methanesulfonyl-phenyl)-thiophen-2-ylmethyl]-benzenesulfonamide,
2-{Isobutyl-[5-(3-methanesulfonyl-phenyl)-thiophen-2-ylmethyl]-sulfamoyl}-benzoic acid methyl ester,
Trifluoro-N-isobutyl-N-[5-(3-methanesulfonyl-phenyl)-thiophen-2-ylmethyl]-methanesulfonamide,
Thiophene-2-sulfonic acid isobutyl-[5-(3-methanesulfonyl-phenyl)-thiophen-2-ylmethyl]-amide,
3-Chloro-2-fluoro-N-isobutyl-N-[5-(3-methanesulfonyl-phenyl)-thiophen-2-ylmethyl]-benzenesulfonamide,
5-Chloro-N-isobutyl-N-[5-(3-methanesulfonyl-phenyl)-thiophen-2-ylmethyl]-2-methoxy-benzenesulfonamide,
5-Fluoro-N-isobutyl-N-[5-(3-methanesulfonyl-phenyl)-thiophen-2-ylmethyl]-2-methyl-benzenesulfonamide,
Butane-1-sulfonic acid isobutyl-[5-(3-methanesulfonyl-phenyl)-thiophen-2-ylmethyl]-amide,
2-Cyano-N-isobutyl-N-[5-(3-methanesulfonyl-phenyl)-thiophen-2-ylmethyl]-benzenesulfonamide,
N-[5-(3-Methanesulfonyl-phenyl)-thiophen-2-ylmethyl]-N-methyl-2-trifluoromethyl-benzenesulfonamide,
N-Ethyl-N-[5-(3-methanesulfonyl-phenyl)-thiophen-2-ylmethyl]-2-trifluoromethyl-benzenesulfonamide,
N-[5-(3-Methanesulfonyl-phenyl)-thiophen-2-ylmethyl]-N-propyl-2-trifluoromethyl-benzenesulfonamide,
N-Isopropyl-N-[5-(3-methanesulfonyl-phenyl)-thiophen-2-ylmethyl]-2-trifluoromethyl-benzenesulfonamide,
N-Isobutyl-N-[5-(3-methanesulfonyl-phenyl)-thiophen-2-ylmethyl]-2-trifluoromethyl-benzenesulfonamide,
N-Cyclopropylmethyl-N-[5-(3-methanesulfonyl-phenyl)-thiophen-2-ylmethyl]-2-trifluoromethyl-benzenesulfonamide,
N-(2-Fluoro-benzyl)-N-[5-(3-methanesulfonyl-phenyl)-thiophen-2-ylmethyl]-2-trifluoromethyl-benzenesulfonamide,
N-(3,5-Dimethyl-isoxazol-4-ylmethyl)-N-[5-(3-methanesulfonyl-phenyl)-thiophen-2-ylmethyl]-2-trifluoromethyl-benzenesulfonamide,
N-[5-(3-Methanesulfonyl-phenyl)-thiophen-2-ylmethyl]-N-(2-methoxy-ethyl)-2-trifluoromethyl-benzenesulfonamide,
N-Cyclobutylmethyl-N-[5-(3-methanesulfonyl-phenyl)-thiophen-2-ylmethyl]-2-trifluoromethyl-benzenesulfonamide,
[[5-(3-Methanesulfonyl-phenyl)-thiophen-2-ylmethyl]-(2-trifluoromethyl-benzenesulfonyl)-amino]-acetic acid tert-butyl ester,
N,N-Diethyl-2-[[5-(3-methanesulfonyl-phenyl)-thiophen-2-ylmethyl]-(2-trifluoromethyl-benzenesulfonyl)-amino]-acetamide,
N-[1,3]Dioxolan-2-ylmethyl-N-[5-(3-methanesulfonyl-phenyl)-thiophen-2-ylmethyl]-2-trifluoromethyl-benzenesulfonamide,
N-[5-(3-Methanesulfonyl-phenyl)-thiophen-2-ylmethyl]-N-(2-pyrrolidin-1-yl-ethyl)-2-trifluoromethyl-benzenesulfonamide, N-[5-(3-Methanesulfonyl-phenyl)-thiophen-2-ylmethyl]-N-(tetrahydro-furan-2-ylmethyl)-2-trifluoromethyl-benzenesulfonamide,
2-Chloro-N-(3-fluoro-3'-methanesulfonyl-biphenyl-4-ylmethyl)-N-isobutyl-benzenesulfonamide,
2-Chloro-N-isobutyl-N-(3'-methanesulfonyl-biphenyl-3-ylmethyl)-benzenesulfonamide,
2-Chloro-N-isobutyl-N-[5-(3-methanesulfonyl-phenyl)-pyridin-3-ylmethyl]-benzenesulfonamide,
2-Chloro-N-isobutyl-N-[5-(3-methanesulfonyl-phenyl)-pyridin-2-ylmethyl]-benzenesulfonamide,
N-Benzyl-N-[5-(4-hydroxymethyl-3-methanesulfonyl-phenyl)-thiophen-2-ylmethyl]-2-trifluoromethyl-benzenesulfonamide,
2-Chloro-N-isobutyl-N-[6-(3-methanesulfonyl-phenyl)-pyridin-2-ylmethyl]-benzenesulfonamide,
2-Chloro-N-isobutyl-N-[2-(3-methanesulfonyl-phenyl)-pyridin-4-ylmethyl]-benzenesulfonamide,
Propane-2-sulfonic acid (3'-methanesulfonyl-biphenyl-3-ylmethyl)-propyl-amide,
Propane-2-sulfonic acid isobutyl-(3'-methanesulfonyl-biphenyl-3-ylmethyl)-amide,
Propane-2-sulfonic acid cyclobutylmethyl-(3'-methanesulfonyl-biphenyl-3-ylmethyl)-amide,
Propane-2-sulfonic acid (2-fluoro-benzyl)-(3'-methanesulfonyl-biphenyl-3-ylmethyl)-amide,
Propane-2-sulfonic acid (4-fluoro-benzyl)-(3'-methanesulfonyl-biphenyl-3-ylmethyl)-amide,
2-Chloro-N-isobutyl-N-[4-(3-aminosulfonyl-phenyl)-thiophen-2-ylmethyl]-benzenesulfonamide,
2-Chloro-N-isobutyl-N-[4-(5-methanesulfonyl-pyridin-3-yl)-thiophen-2-ylmethyl]-benzenesulfonamide,
2-Chloro-N-isobutyl-N-[4-(3-tert-butylaminosulfonyl-phenyl)-thiophen-2-ylmethyl]-benzenesulfonamide,
N-Isobutyl-N-[5-(3-methanesulfonyl-phenyl)-thiophen-2-ylmethyl]-C-phenyl-methanesulfonamide, and
C-Cyclohexyl-N-isobutyl-N-[5-(3-methanesulfonyl-phenyl)-thiophen-2-ylmethyl]-methanesulfonamide,
and pharmaceutically acceptable salts and esters thereof.

Particularly preferred compounds of formula (I) are those selected from the group consisting of
2-Fluoro-N-isobutyl-N-[5-(3-methanesulfonyl-phenyl)-thiophen-2-ylmethyl]-benzenesulfonamide,
Trifluoro-N-isobutyl-N-[5-(3-methanesulfonyl-phenyl)-thiophen-2-ylmethyl]-methanesulfonamide,
2-Cyano-N-isobutyl-N-[5-(3-methanesulfonyl-phenyl)-thiophen-2-ylmethyl]-benzenesulfonamide,
N-Isopropyl-N-[5-(3-methanesulfonyl-phenyl)-thiophen-2-ylmethyl]-2-trifluoromethyl-benzenesulfonamide,
N-Cyclopropylmethyl-N-[5-(3-methanesulfonyl-phenyl)-thiophen-2-ylmethyl]-2-trifluoromethyl-benzenesulfonamide,
2-Chloro-N-(3-fluoro-3'-methanesulfonyl-biphenyl-4-ylmethyl)-N-isobutyl-benzenesulfonamide,
2-Chloro-N-isobutyl-N-[5-(3-methanesulfonyl-phenyl)-pyridin-2-ylmethyl]-benzenesulfonamide, and
Propane-2-sulfonic acid (2-fluoro-benzyl)-(3'-methanesulfonyl-biphenyl-3-ylmethyl)-amide,
and pharmaceutically acceptable salts and esters thereof.

It will be appreciated that the compounds of general formula (I) in this invention may be derivatised at functional groups to provide derivatives which are capable of conversion back to the parent compound in vivo.

The invention further relates to a process for the manufacture of compounds of formula (I) as defined above, which process comprises a) reacting a compound of formula (II)

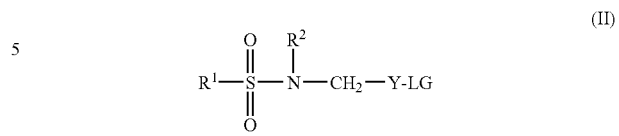

with a compound of formula $R^3$-M, or b) reacting a compound of formula (III)

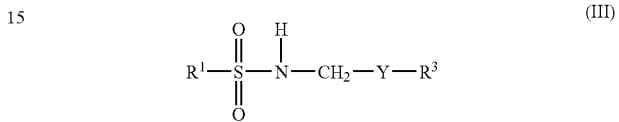

with a compound $R^2X$, or c) reacting a compound of formula (IV)

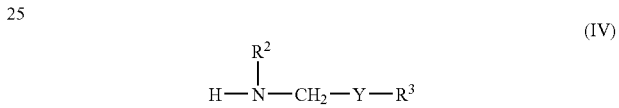

with a compound $R^1SO_2Cl$, wherein $R^1$, $R^2$, $R^3$ and Y are as defined above; LG is Cl, Br, I, OMs, OTs or OTf; M is boronic acid or boronic acid ester; X is Cl, Br, I, OMs, OTs, OTf or OH.

The reactions given above can be carried out under conditions well known to the person skilled in the art, e.g. as described below in context with schemes 1, 2, 3 and 4.

The present invention also relates to compounds of formula (I) as defined above, when prepared by a process as described above.

The compounds of formula (I) can be prepared by methods known in the art or as described below in schemes 1 to 4. All starting materials are either commercially available, described in the literature or can be prepared by methods well known in the art. Unless otherwise indicated, $R^1$, $R^2$, $R^3$ and Y are as defined above.

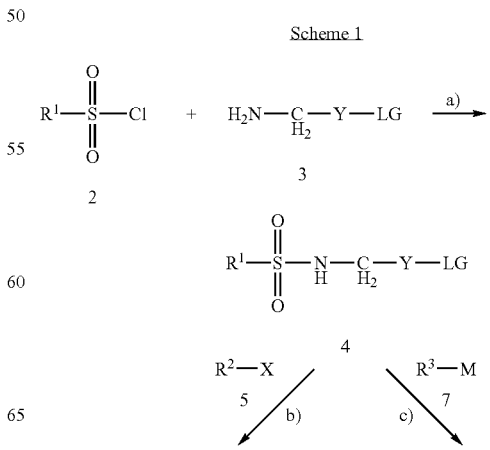

Scheme 1

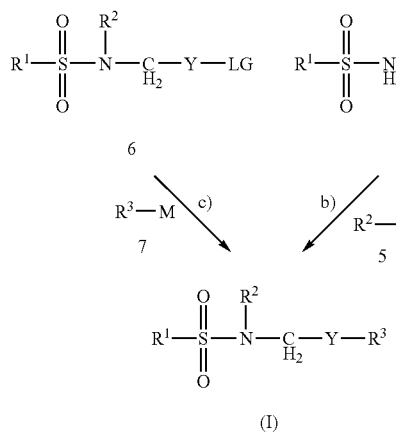

X = Cl, Br, I, OMs, OTs, OTf, OH
LG = Cl, Br, I, OMs, OTs, OTf
M = B(OH)$_2$, B(OR)$_2$

Compounds of formula (I) can be prepared according to the methods described in scheme 1: Sulfonylchlorides 2 as well as amines 3 are either commercially available, described in the literature or can be prepared by methods well known to a person skilled in the art. Sulfonylation of 3 can be achieved by treatment with sulfonylchlorides 2 in solvents such as dichloromethane, tetrahydrofuran, N,N-dimethylacetamide or dioxane in the presence of bases such as N,N-diisopropyl-ethylamine, triethylamine or pyridine optionally in the presence of DMAP at 0° C. to room temperature (step a). The sulfonamides 4 can be alkylated by treatment with alkylating agents 5 in which X is a leaving group such as Cl, Br, I, OMs, OTs, or OTf. These reactions are performed in the presence of a base such as Cs$_2$CO$_3$, K$_2$CO$_3$, NaH or N,N-diisopropyl-ethylamine in inert solvents such as acetone, dioxane, N,N-dimethylformamide or N,N-dimethylacetamide optionally in the presence of KI, NaI or tetrabutylammonium iodide at temperatures between 0° C. and reflux of the solvent (step b). Alternatively, sulfonamides 4 can be alkylated with agents 5 in which X represents a hydroxy group using Mitsunobu conditions, that means treatment with a dialkylazodicarboxylate such as diethylazodicarboxylate, diisopropylazodicarboxylate or di-tert-butyldiazodicarboxylate and with triphenylphosphine in a solvent such as tetrahydrofuran at 0° C. to room temperature. Compounds 6 in which LG represents a leaving group such as Cl, Br, I, OMs, OTs, or OTf can be coupled with suitably substituted aryl or heteroaryl metal species of formula 7, preferably boronic acids or boronic acid esters, such as e.g. boronic acid methyl esters, boronic acid ethylene glycol esters or boronic acid pinacol esters, in the presence of a suitable catalyst, preferably a palladium catalyst such as dichloro[1,1'-bis(diphenylphosphino)ferrocene]palladium (II) or tetrakis(triphenylphosphine)palladium (0) and a base, preferably sodium carbonate, potassium fluoride, potassium carbonate or triethylamine in solvents such as dioxane, water, toluene, N,N-dimethylformamide or mixtures thereof to give compounds of formula (I) (step c). Alternatively, the order of steps can be reversed: The sulfonamides 4 can first be coupled in a Suzuki reaction to suitably substituted aryl or heteroaryl metal species of formula 7 as described above, to give compounds of formula 8, followed by alkylation with compounds 5 as described above for the synthesis of compounds 6 (steps c, b).

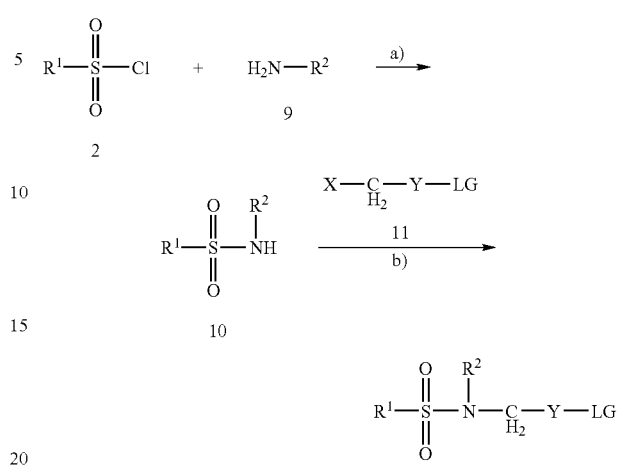

X = Cl, Br, I, OMs, OTs, OTf, OH
LG = Cl, Br, I, OMs, OTs, OTf

An alternative synthesis of the intermediates 6 is described in scheme 2: Treatment of amines 9 with sulfonylchlorides 2 in solvents such as dichloromethane, tetrahydrofuran, N,N-dimethylacetamide or dioxane in the presence of bases such as N,N-diisopropyl-ethylamine, triethylamine or pyridine optionally in the presence of DMAP at 0° C. to room temperature provides sulfonamides 10 (step a). The sulfonamides 10 can be alkylated by treatment with alkylating agents 11 in which X is a leaving group such as Cl, Br, I, OMs, OTs, or OTf. These reactions are performed in the presence of a base such as Cs$_2$CO$_3$, K$_2$CO$_3$, NaH or N,N-diisopropyl-ethylamine in inert solvents such as acetone, dioxane, N,N-dimethylformamide or N,N-dimethylacetamide optionally in the presence of KI, NaI or tetrabutylammonium iodide at temperatures between 0° C. and reflux of the solvent (step b). Alternatively, sulfonamides 10 can be alkylated with agents 11 in which X represents a hydroxy group using Mitsunobu conditions, that means treatment with a dialkylazodicarboxylate such as diethylazodicarboxylate, diisopropylazodicarboxylate or di-tert-butyldiazodicarboxylate and with triphenylphosphine in a solvent such as tetrahydrofuran at 0° C. to room temperature.

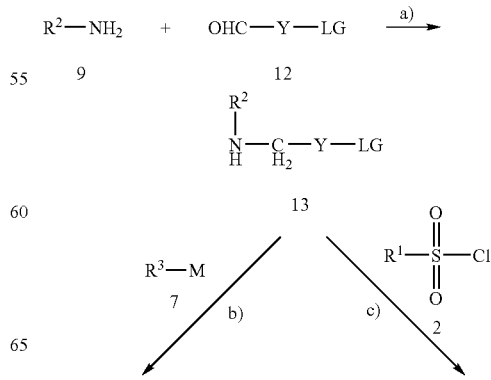

-continued

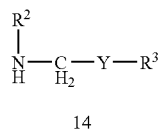 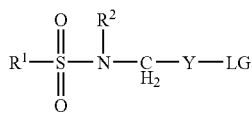

14 5 6

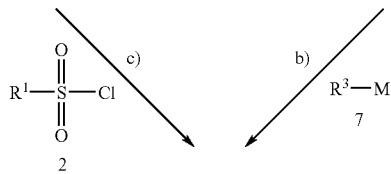

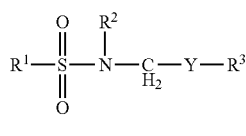

(I)

LG = Cl, Br, I, OMs, OTs, OTf
M = B(OH)₂, B(OR)₂

Compounds of formula (I) can also be prepared according to the methods described in scheme 3:

Treatment of amines 9 with aldehydes 12 in solvents such as methanol, ethanol or dichloromethane optionally in the presence of a drying agent such as magnesium sulfate followed by treatment with a reducing agent such as sodium borohydride or sodium cyanoborohydride gives amines 13 (step a). Compounds 13 in which LG represents a leaving group such as Cl, Br, I, OMs, OTs, or OTf can be coupled with suitably substituted aryl or heteroaryl metal species of formula 7, preferably boronic acids or boronic acid esters, in the presence of a suitable catalyst, preferably a palladium catalyst such as dichloro[1,1'-bis(diphenylphosphino)ferrocene]palladium (II) or tetrakis(triphenylphosphine)palladium (0) and a base, preferably sodium carbonate, potassium fluoride, potassium carbonate or triethylamine in solvents such as dioxane, water, toluene, N,N-dimethylformamide or mixtures thereof to give compounds of formula 14 (step b). Amines 14 can be reacted with sulfonylchlorides 2 in solvents such as dichloromethane, tetrahydrofuran, N,N-dimethylacetamide or dioxane in the presence of bases such as N,N-diisopropyl-ethylamine, triethylamine or pyridine optionally in the presence of DMAP at 0° C. to room temperature to give compounds (I) (step c). Alternatively, the order of steps can be reversed: Compounds 13 can first be reacted with sulfonylchlorides 2 to give compounds 6 followed by a Suzuki reaction to give compounds (I) (steps c,b).

Scheme 4

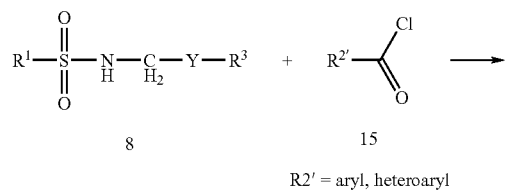

R2' = aryl, heteroaryl

-continued

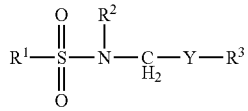

(I)

R2 = aryl-C(O), heteroaryl-C(O)

The synthesis of compounds (I) in which $R^2$ represents aryl-C(O) or heteroaryl-C(O) is described in scheme 4: Treatment of sulfonamides 8 with aryl- or heteroarylcarbonyl chlorides in the presence of a base such as N,N-diisopropyl-ethylamine, triethylamine or sodium hydride in solvents such as dichloromethane, tetrahydrofuran, N,N-dimethylacetamide or dioxane at temperatures from 0° C. to room temperature provides compounds (I).

As will be understood by those skilled in the art, for the preparation of enantiomerically pure products, enantiomerically pure starting materials should be used. In addition the compounds of formula (I) might be separated into the enantiomerically pure compounds by chromatography on a chiral HPLC column, chromatography with a chiral eluant or by crystallization via diastereomeric salts.

The conversion of a compound of formula (I) into a pharmaceutically acceptable salt can be carried out by treatment of such a compound with an inorganic acid, for example a hydrohalic acid, such as, for example, hydrochloric acid or hydrobromic acid, or other inorganic acids such as sulfuric acid, nitric acid, phosphoric acid etc., or with an organic acid, such as, for example, acetic acid, citric acid, maleic acid, fumaric acid, tartaric acid, methanesulfonic acid or p-toluenesulfonic acid. The salts with an inorganic or organic acid can be obtained by standard methods known to the person skilled in the art, e.g. by dissolving the compound of formula (I) in a suitable solvent such as e.g. dioxane or THF and adding an appropriate amount of the corresponding acid. The products can conveniently be isolated by filtration or by chromatography. If an acidic group is present, the corresponding salts can be prepared from the compounds of formula (I) by treatment with physiologically compatible bases. One possible method to form such a salt is e.g. by addition of 1/n equivalents of a basic salt such as e.g. $M(OH)_n$, wherein M=metal or ammonium cation and n=number of hydroxide anions, to a solution of the compound in a suitable solvent (e.g. ethanol, ethanol-water mixture, tetrahydrofuran-water mixture) and to remove the solvent by evaporation or lyophilisation.

The conversion of compounds of formula (I) into pharmaceutically acceptable esters can be carried out e.g. by treatment of hydroxy groups present in the molecules with a carboxylic acid such as acetic acid, with a condensating reagent such as benzotriazol-1-yloxytris(dimethylamino)phosphonium hexafluorophosphate (BOP), N,N-dicylohexylcarbodiimide (DCC), N-(3-dimethylaminopropyl)-N'-ethylcarbodiimide hydrochloride (EDCI) or O-(1,2-dihydro-2-oxo-1-pyridyl)-N,N,N,N-tetra-methyluronium-tetrafluorborate (TPTU) to produce the carboxylic ester.

Insofar as their preparation is not described in the examples, the compounds of formula (I) as well as all intermediate products can be prepared according to analogous methods or according to the methods set forth above. Starting materials are commercially available or known in the art.

As described above, the novel compounds of the present invention have been found to bind to and selectively activate LXR alpha and LXR beta or coactivate LXR alpha and LXR beta. Consequently, cholesterol absorption is reduced, HDL cholesterol is increased, and inflammatory atherosclerosis is reduced. They can therefore be used in the treatment and prophylaxis of diseases in a human being (or animal) which are modulated by LXR alpha and/or LXR beta agonists. Such diseases include increased lipid and cholesterol levels, particularly low HDL-cholesterol, high LDL-cholesterol, atherosclerotic diseases, diabetes, particularly non-insulin dependent diabetes mellitus, metabolic syndrome, dyslipidemia, sepsis, and inflammatory diseases such as colitis, pancreatitis, cholestasis/fibrosis of the liver, psoriasis and other inflammatory diseases of the skin, and diseases that have an inflammatory component such as Alzheimer's disease or impaired/improvable cognitive function. Moreover, the novel compounds of the present invention can be used for treatment of infectious diseases such as HIV as well as cancer and for prophylaxis of age-related and inherited (e.g. Stargardt's disease) forms of macular degeneration.

The invention therefore also relates to pharmaceutical compositions comprising a compound as defined above and a pharmaceutically acceptable carrier and/or adjuvant.

The invention likewise embraces compounds as described above for use as therapeutically active substances, especially as therapeutically active substances for the treatment and/or prophylaxis of diseases in a human being (or animal) which are modulated by LXR alpha and/or LXR beta agonists, particularly as therapeutically active substances for the treatment and/or prophylaxis of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

In another preferred embodiment, the invention relates to a method for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease, which method comprises administering a compound as defined above to a human being or animal.

The invention also embraces the use of compounds as defined above for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease.

The invention also relates to the use of compounds as described above for the preparation of medicaments for the therapeutic and/or prophylactic treatment of diseases which are modulated by LXR alpha and/or LXR beta agonists, particularly for the therapeutic and/or prophylactic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease. Such medicaments comprise a compound as described above.

Prevention and/or treatment of increased lipid levels, increased cholesterol levels, atherosclerotic diseases, dyslipidemia, or diabetes is the preferred indication, particularly prevention and/or treatment of increased lipid levels, increased cholesterol levels, atherosclerotic diseases, or dyslipidemia, especially prevention and/or treatment of atherosclerotic diseases or dyslipidemia.

Diabetes, particularly non-insulin dependent diabetes mellitus, is another preferred disease. The following tests were carried out in order to determine the activity of the compounds of the present invention. Background information on the performed assays can be found in: Nichols J S et al. "Development of a scintillation proximity assay for peroxisome proliferator-activated receptor gamma ligand binding domain", Anal Biochem. 1998, 257: 112-119. Mammalian expression vectors were constructed to express full-length human LXR alpha and LXR beta. Bacterial expression vectors were constructed to produce tagged versions of the ligand binding domains (LBD) of human LXR alpha (aa 164 to 447) and human LXR beta (aa 155 to 460). To accomplish this, the portions of the sequences encoding the LBDs were amplified from the full-length clones by PCR and then subcloned into the plasmid vectors. Final clones were verified by DNA sequence analysis (Willy et al., Genes Dev. 1995, 9:1033-45; Song et al., Proc Natl Acad Sci USA. 1994, 91:10809-13).

Induction, expression, and purification of LBD proteins were performed in *E. coli* strain BL21 (pLysS) cells by standard methods (Ref: Current Protocols in Molecular Biology, Wiley Press, edited by Ausubel et al).

Radioligand Binding Assay

LXR alpha and LXR beta receptor binding were assayed in buffer consisting of 50 mM HEPES, pH 7.4, 10 mM NaCl, 5 mM $MgCl_2$. For each 96-well reaction, 500 ng of LXRα-LBD or 700 ng of LXR beta-LBD proteins were bound to 80 μg or 40 μg SPA beads respectively, in a final volume of 50 μl by shaking. The resulting slurry was incubated for 1 h at RT and centrifuged for 2 min at 1300×g. The supernatant containing unbound protein was removed, and the semi-dry pellet containing the receptor-coated beads was re-suspended in 50 μl of buffer. Radioligand (eg. 100,000 dpm of (N-(2,2,2-trifluoroethyl)-N-[4-(2,2,2-trifluoro-1-hydroxy-1-trifluoromethylethyl)-phenyl]-benzenesulfonamide)) was added, and the reaction incubated at RT for 1 h in the presence of test compounds, and then scintillation proximity counting was performed. All binding assays were performed in 96-well plates and the amount of bound ligand was measured on a Packard TopCount using OptiPlates (Packard). Dose response curves were measured within a range of concentration from $10^{-10}$ M to $10^{-4}$ M.

Luciferase Transcriptional Reporter Gene Assays

Baby hamster kidney cells (BHK21 ATCC CCL10) were grown in DMEM medium containing 10% FBS at 37° C. in a 95% $O_2$:5% $CO_2$ atmosphere. Cells were seeded in 6-well plate a density of $10^5$ Cells/well and then batch-transfected with either the full-length-LXRα or full-length-LXRβ expression plasmids plus a reporter plasmid expressing luciferase under the control of LXR response elements. Transfection was accomplished with the Fugene 6 reagent (Roche Molecular Biochemicals) according to the suggested protocol. Six hours following transfection, the cells were harvested by trypsinization and seeded in 96-well plates at a density of $10^4$ cells/well. After 24 hours to allow attachment of cells, the medium was removed and replaced with 100 μl of phenol red-free medium containing the test substances or control ligands (final DMSO concentration: 0.1%). Following incubation of the cells for 24 hours with substances, 50 μl of the supernatant was discarded and then 50 μl of Luciferase Constant-Light Reagent (Roche Molecular Biochemicals) was added to lyse the cells and initiate the luciferase reaction. Luminescence, as a measure of luciferase activity, was detected in a Packard TopCount. Transcriptional activation in the presence of a test substance was expressed as fold-change in luminescence compared to that of cells incubated in the absence of the substance. $EC_{50}$ values were calculated using the XLfit program (ID Business Solutions Ltd. UK).

The compounds according to formula (I) have an activity in at least one of the above assays (EC50 or IC50) of 1 nM to 100 μM, preferably 1 nM to 10 μM, more preferably 1 nM to 1 μM.

For example, the following compounds showed the following IC50 values in the binding assay:

| Example | LXRbeta Binding IC$_{50}$ [μmol/l] | LXRalpha Binding IC$_{50}$ [μmol/l] |
|---|---|---|
| 1 | 0.165 | 0.205 |
| 2 | 0.1255 | 0.17 |
| 3 | 5.41 | 5.715 |
| 4 | 0.1225 | 0.685 |
| 5 | 0.1025 | 1.17 |
| 6 | 0.046 | 1.57 |
| 7 | 1.51 | 4.275 |
| 8 | 0.56 | 0.925 |
| 9 | 0.98 | 2.14 |
| 10 | 0.0565 | 2.7 |
| 11 | 0.17 | 8.775 |
| 12 | 0.12 | 27.325 |
| 13 | 0.0405 | 3.49 |
| 14 | 0.0022 | 0.068 |
| 15 | 7.06 | 48.735 |
| 16 | 2.865 | 24.95 |
| 17 | 0.028 | 2.215 |
| 18 | 0.082 | 1.445 |
| 19 | 0.059 | 2.63 |
| 20 | 0.27 | 3.75 |
| 21 | 0.14 | 0.605 |
| 22 | 0.0225 | 1.375 |
| 23 | 0.019 | 1.525 |
| 24 | 0.0285 | 0.165 |
| 25 | 0.08 | 2.75 |
| 26 | 0.098 | 15.86 |
| 27 | 2.605 | 29.2 |
| 28 | 0.44 | 19.905 |
| 29 | 0.104 | 2.46 |
| 30 | 0.47 | 7.865 |
| 31 | 0.085 | 1.455 |
| 32 | 0.106 | 0.845 |
| 33 | 0.0066 | 0.0135 |
| 34 | 0.083 | 0.0605 |
| 35 | 0.1165 | 0.975 |
| 36 | 0.0175 | 0.665 |
| 37 | 0.0115 | 0.0175 |
| 38 | 0.16 | 2.41 |
| 39 | 0.047 | 0.82 |
| 40 | 0.285 | 10.66 |
| 41 | 0.037 | 0.79 |
| 42 | 0.0068 | 0.0082 |
| 43 | 0.019 | 0.026 |
| 44 | 0.03 | 3.445 |
| 45 | 0.0023 | 0.425 |
| 46 | 0.0006 | 0.0034 |
| 47 | 0.0495 | 1.48 |
| 48 | 0.15 | 7.86 |
| 49 | 1.56 | 20.15 |
| 50 | 0.805 | 2.27 |
| 51 | 0.28 | 1.635 |
| 52 | 0.0335 | 0.61 |
| 53 | 0.255 | 2.8 |
| 54 | 0.0074 | 0.0845 |
| 55 | 0.083 | 2.53 |
| 56 | 39.075 | 17.71 |
| 57 | 0.45 | 28.915 |
| 58 | 1.335 | 31.675 |

These results have been obtained by using the foregoing test.

The compounds of formula I and/or their pharmaceutically acceptable salts can be used as medicaments, e.g. in the form of pharmaceutical preparations for enteral, parenteral or topical administration. They can be administered, for example, perorally, e.g. in the form of tablets, coated tablets, dragées, hard and soft gelatine capsules, solutions, emulsions or suspensions, rectally, e.g. in the form of suppositories, parenterally, e.g. in the form of injection solutions or suspensions or infusion solutions, or topically, e.g. in the form of ointments, creams or oils. Oral administration is preferred.

The production of the pharmaceutical preparations can be effected in a manner which will be familiar to any person skilled in the art by bringing the described compounds of formula I and/or their pharmaceutically acceptable salts, optionally in combination with other therapeutically valuable substances, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragées and hard gelatine capsules. Suitable carrier materials for soft gelatine capsules are, for example, vegetable oils, waxes, fats and semi-solid and liquid polyols (depending on the nature of the active ingredient no carriers might, however, be required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavour-improving agents, salts for varying the osmotic pressure, buffer substances, solubilizers, colorants and masking agents and antioxidants come into consideration as pharmaceutical adjuvants.

The dosage (therapeutically effective amount) of the compounds of formula I can vary within wide limits depending on the disease to be controlled, the age and the individual condition of the patient and the mode of administration, and will, of course, be fitted to the individual requirements in each particular case. For adult patients a daily dosage of about 1 to 2000 mg, especially about 1 to 500 mg, comes into consideration. Depending on severity of the disease and the precise pharmacokinetic profile the compound could be administered with one or several daily dosage units, e.g. in 1 to 3 dosage units.

The pharmaceutical preparations conveniently contain about 1-500 mg, preferably 1-200 mg, of a compound of formula I.

The following examples serve to illustrate the present invention in more detail. They are, however, not intended to limit its scope in any manner.

EXAMPLES

Example 1

N-Benzyl-N-[5-(3-methanesulfonyl-phenyl)-thiophen-2-ylmethyl]-2-trifluoromethyl-benzenesulfonamide Step 1: To a stirred suspension of 1-(5-bromo-2-thienyl)-methanamine (0.5 g) in dichloromethane (8 mL) were added 2-(trifluoromethyl)-benzenesulfonyl chloride (0.67 g) and N-ethyl-diisopropylamine (0.37 g) at 0° C. After stirring for 10 min, the ice bath was removed and the mixture was stirred for 40 min. The reaction mixture was diluted with dichloromethane and washed with 0.5 M HCl and with water. The organic phase was dried ($MgSO_4$), filtered and concentrated. The residue was suspended in cyclohexane. The solid was collected by filtration and dried to give N-(5-bromo-thiophen-2-ylmethyl)-2-trifluoromethyl-benzenesulfonamide (0.596 g) as a colorless solid. MS: 417.1 ($[M+NH_4]^+$)

Step 2: To a stirred solution of N-(5-bromo-thiophen-2-ylmethyl)-2-trifluoromethyl-benzenesulfonamide (0.594 g) in N,N-dimethylacetamide (4 mL) was added NaH (dispersion, ca 55% in oil, 0.039 g) at 0° C. After stirring for 5 min, the ice bath was removed and the mixture was stirred for 50 min. Benzyl bromide (0.28 g) was added and the mixture was stirred overnight at r.t. Water was added and the mixture was extracted with ethyl acetate. The organic phase was dried ($MgSO_4$), filtered and concentrated under reduced pressure. The product was purified by chromatography ($SiO_2$, cyclohexane to cyclohexane/ethyl acetate 2:1) to give N-benzyl-N-(5-bromo-thiophen-2-ylmethyl)-2-trifluoromethyl-benzenesulfonamide (0.555 g) as a colorless solid. MS: 490 ($[M+H]^+$)

Step 3: Under argon to a stirred suspension of N-benzyl-N-(5-bromo-thiophen-2-ylmethyl)-2-trifluoromethyl-benzenesulfonamide (89 mg) and (3-methylsulfonylphenyl)-boronic acid (55 mg) in dioxane (0.5 mL), water (0.3 mL) and a 2 M $Na_2CO_3$ solution (0.27 mL) was added dichloro[1,1'-bis (diphenylphosphino)ferrocene]palladium dichloromethane adduct (7 mg). The mixture was stirred for 3.5 h at 80° C. Ethyl acetate was added and the mixture was washed with water. The organic phase was dried ($MgSO_4$), filtered and concentrated under reduced pressure. The product was purified by chromatography ($SiO_2$, cyclohexane/ethyl acetate 7:3) to give N-benzyl-N-[5-(3-methanesulfonyl-phenyl)-thiophen-2-ylmethyl]-2-trifluoromethyl-benzenesulfonamide (88 mg) as a light yellow oil. MS: 582.6 ($[M+NH_4]^+$)

Example 2

N-Benzyl-N-[5-(3-methanesulfonylamino-phenyl)-thiophen-2-ylmethyl]-2-trifluoromethyl-benzenesulfonamide In analogy to example 1, step 3, N-benzyl-N-(5-bromo-thiophen-2-ylmethyl)-2-trifluoromethyl-benzenesulfonamide was reacted with (3-methylsulfonylaminophenyl)-boronic acid, $Na_2CO_3$ and dichloro[1,1'-bis (diphenylphosphino)ferrocene]palladium dichloromethane adduct in dioxane/water to give N-benzyl-N-[5-(3-methanesulfonylamino-phenyl)-thiophen-2-ylmethyl]-2-trifluoromethyl-benzenesulfonamide as a light yellow foam. MS: 598.3 ($[M+NH_4]^+$)

Example 3

N-Benzyl-N-[5-(3-methanesulfonyl-phenyl)-[1,3,4]oxadiazol-2-ylmethyl]-2-trifluoromethyl-benzenesulfonamide Step 1: To a stirred solution of 2-trifluoromethylbenzenesulfonyl chloride (3.8 g) in dichloromethane (100 mL) under argon was added pyridine (14 mL). A solution of N-benzylglycine ethylester (2 g) in dichloromethane (40 mL) was added slowly. The mixture was stirred at r.t. overnight and then concentrated under reduced pressure. The residue was dissolved in dichloromethane and washed with water. The organic phase was dried ($MgSO_4$), filtered and concentrated under reduced pressure. The product was purified by chromatography ($SiO_2$, cyclohexane to cyclohexane/ethyl acetate 1:1) to give [benzyl-(2-trifluoromethyl-benzenesulfonyl)-amino]-acetic acid ethyl ester (2.61 g) as a colorless oil. MS: 402.1 ($[M+H]^+$)

Step 2: To a stirred solution of [benzyl-(2-trifluoromethyl-benzenesulfonyl)-amino]-acetic acid ethyl ester (2.52 g) in ethanol (15 mL) was added hydrazine monohydrate (1.60 g). The mixture was stirred for 5 h at r.t. and for 22 h at 50° C. The mixture was concentrated under reduced pressure. The residue was taken up in ethyl acetate and washed with water. The organic phase was dried ($MgSO_4$), filtered and concentrated under reduced pressure to give N-benzyl-N-hydrazinocarbonylmethyl-2-trifluoromethyl-benzenesulfonamide (2.27 g) as a colorless oil. MS: 388.4 ($[M+H]^+$)

Step 3: To a stirred solution of 3-methylsulfonylbenzoic acid (60 mg) in N,N-dimethylacetamide (1.3 mL) was added 1,1'-carbonyl-diimidazole (52 mg). The mixture was stirred at 50° C. for 20 min. After cooling to r.t., N-benzyl-N-hydrazinocarbonylmethyl-2-trifluoromethyl-benzenesulfonamide (100 mg) was added and the mixture was stirred at 100° C. overnight. After cooling to r.t. the mixture was diluted with ethyl acetate and washed with water. The organic phase was dried ($MgSO_4$), filtered and concentrated under reduced pressure. The product was purified by chromatography ($SiO_2$, dichloromethane to dichloromethane/methanol 95:5) to give N-benzyl-N-{2-[N'-(3-methanesulfonyl-benzoyl)-hydrazino]-2-oxo-ethyl}-2-trifluoromethyl-benzenesulfonamide (111 mg) as a colorless oil. MS: 570.3 ($[M+H]^+$)

Step 4: A mixture of N-benzyl-N-{2-[N'-(3-methanesulfonyl-benzoyl)-hydrazino]-2-oxo-ethyl}-2-trifluoromethyl-benzenesulfonamide (111 mg) and phosphorus oxychloride (1.5 g) was stirred for 18 h at 110° C. and then was concentrated under reduced pressure. The product was purified by chromatography (SiO$_2$, cyclohexane/ethyl acetate 1:1 to ethyl acetate) to give N-benzyl-N-[5-(3-methanesulfonyl-phenyl)-[1,3,4]oxadiazol-2-ylmethyl]-2-trifluoromethyl-benzenesulfonamide (74 mg) as a colorless foam. MS: 552.3 ([M+H]$^+$)

Example 4

N-Benzyl-2-chloro-N-[5-(3-methanesulfonyl-phenyl)-thiophen-2-ylmethyl]-benzenesulfonamide Step 1: To a stirred suspension of 1-(5-bromo-2-thienyl) methanamine (1.00 g) in dichloromethane (15 mL) were slowly added 2-chlorobenzenesulfonyl chloride (1.18 g) and N,N-diisopropyl ethyl amine (0.76 g) at 0° C. After 15 min the ice bath was removed and the mixture was stirred at r.t. for 1.5 h. The mixture was diluted with dichloromethane and washed with 0.5 M HCl and with water. The organic phase was dried (MgSO$_4$), filtered and concentrated under reduced pressure. The product was purified by chromatography (SiO$_2$, cyclohexane/ethyl acetate 95:5 to ethyl acetate) to give N-(5-bromo-thiophen-2-ylmethyl)-2-chloro-benzenesulfonamide (0.83 g) as a colorless solid. MS: 363.9 ([M–H]$^-$)

Step 2: In analogy to example 1, step 3, N-(5-bromo-thiophen-2-ylmethyl)-2-chloro-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-[5-(3-methanesulfonyl-phenyl)-thiophen-2-ylmethyl]-benzenesulfonamide as an off-white solid. MS: 440.3 ([M–H]$^-$)

Step 3: In analogy to example 1, step 2, 2-chloro-N-[5-(3-methanesulfonyl-phenyl)-thiophen-2-ylmethyl]-benzenesulfonamide was reacted with sodium hydride in N,N-dimethylacetamide at 0° C. followed by reaction with benzyl bromide at r.t. overnight to give N-benzyl-2-chloro-N-[5-(3-methanesulfonyl-phenyl)-thiophen-2-ylmethyl]-benzenesulfonamide as a colorless solid. MS: 549.3 ([M+NH$_4$]$^+$)

Example 5

2-Chloro-N-isobutyl-N-[5-(3-methanesulfonyl-phenyl)-thiophen-2-ylmethyl]-benzenesulfonamide In analogy to example 1, step 2, 2-chloro-N-[5-(3-methanesulfonyl-phenyl)-thiophen-2-ylmethyl]-benzenesulfonamide (example 4, step 2) was reacted with sodium hydride in N,N-dimethylacetamide at 0° C. followed by reaction with 1-bromo-2-methylpropane at r.t. overnight to give 2-chloro-N-isobutyl-N-[5-(3-methanesulfonyl-phenyl)-thiophen-2-ylmethyl]-benzenesulfonamide as an off-white solid. MS: 515.3 ([M+NH$_4$]$^+$)

Example 6

N-Benzoyl-2-chloro-N-[5-(3-methanesulfonyl-phenyl)-thiophen-2-ylmethyl]-benzenesulfonamide To a stirred solution of 2-chloro-N-[5-(3-methanesulfonyl-phenyl)-thiophen-2-ylmethyl]-benzenesulfonamide (example 4, step 2, 60 mg) in dichloromethane (0.5 mL) were added N,N-diisopropyl ethyl amine (21 mg) and benzoyl chloride (20 mg) at 0° C. The mixture was stirred at r.t. overnight. Ice cold water was added and the mixture was extracted with ethyl acetate. The organic phase was dried (MgSO$_4$), filtered and concentrated under reduced pressure. The product was purified by chromatography (SiO$_2$, cyclohexane/ethyl acetate 1:0 to 0:1) to give N-benzoyl-2-chloro-N-[5-(3-methanesulfonyl-phenyl)-thiophen-2-ylmethyl]-benzenesulfonamide (76 mg) as a colorless solid. MS: 568.2 ([M+Na]$^+$)

Example 7

N-Benzyl-3-chloro-N-[5-(3-methanesulfonyl-phenyl)-thiophen-2-ylmethyl]-benzenesulfonamide Step 1: In analogy to example 4, step 1, 1-(5-bromo-2-thienyl)methanamine was reacted with 3-chlorobenzenesulfonyl chloride and N,N-diisopropyl ethyl amine in dichloromethane to give N-(5-bromo-thiophen-2-ylmethyl)-3-chloro-benzenesulfonamide as a colorless solid. MS: 363.9 ([M–H]$^-$)

Step 2: In analogy to example 1, step 3, N-(5-bromo-thiophen-2-ylmethyl)-3-chloro-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 3-chloro-N-[5-(3-methanesulfonyl-phenyl)-thiophen-2-ylmethyl]-benzenesulfonamide as an off-white solid. MS: 440.3 ([M–H]$^-$)

Step 3: In analogy to example 1, step 2, 3-chloro-N-[5-(3-methanesulfonyl-phenyl)-thiophen-2-ylmethyl]-benzenesulfonamide was reacted with sodium hydride in N,N-dimethylacetamide at 0° C. followed by reaction with benzyl bromide at r.t. overnight to give N-benzyl-3-chloro-N-[5-(3-methanesulfonyl-phenyl)-thiophen-2-ylmethyl]-benzenesulfonamide as an off-white solid. MS: 549.3 ([M+NH$_4$]$^+$)

Example 8

3-Chloro-N-isobutyl-N-[5-(3-methanesulfonyl-phenyl)-thiophen-2-ylmethyl]-benzenesulfonamide In analogy to example 1, step 2, 3-chloro-N-[5-(3-methanesulfonyl-phenyl)-thiophen-2-ylmethyl]-benzenesulfonamide (example 7, step 2) was reacted with sodium hydride in N,N-dimethylacetamide at 0° C. followed by reaction with 1-bromo-2-methylpropane at r.t. overnight to give 3-chloro-N-isobutyl-N-[5-(3-methanesulfonyl-phenyl)-thiophen-2-ylmethyl]-benzenesulfonamide as a colorless solid. MS: 515.3 ([M+NH$_4$]$^+$)

Example 9

N-Benzoyl-3-chloro-N-[5-(3-methanesulfonyl-phenyl)-thiophen-2-ylmethyl]-benzenesulfonamide In analogy to example 6, 3-chloro-N-[5-(3-methanesulfonyl-phenyl)-thiophen-2-ylmethyl]-benzenesulfonamide (example 7, step 2) was reacted with benzoyl chloride and N,N-diisopropyl ethyl amine in dichloromethane to give N-benzoyl-3-chloro-N-[5-(3-methanesulfonyl-phenyl)-thiophen-2-ylmethyl]-benzenesulfonamide as a colorless solid. MS: 563.2 ([M+NH$_4$]$^+$)

Example 10

N-Benzyl-2-chloro-N-[2-(3-methanesulfonyl-phenyl)-thiazol-5-ylmethyl]-benzenesulfonamide Step 1: In analogy to example 1, step 1, 2-bromo-5-aminomethyl-thiazole hydrochloride was reacted with 2-chlorobenzenesulfonylchloride and N,N-diisopropyl ethyl amine in dichloromethane to give N-(2-bromo-thiazol-5-ylmethyl)-2-chloro-benzenesulfonamide as an off-white solid. MS: 367.0 ([M+H]$^+$)

Step 2: In analogy to example 1, step 3, N-(2-bromo-thiazol-5-ylmethyl)-2-chloro-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-[2-(3-methanesulfonyl-phenyl)-thiazol-5-ylmethyl]-benzenesulfonamide as a light yellow oil. MS: 443.3 ([M+H]$^+$)

Step 3: To a stirred solution of 2-chloro-N-[2-(3-methanesulfonyl-phenyl)-thiazol-5-ylmethyl]-benzenesulfonamide (30 mg) in N,N-dimethylacetamide (0.6 mL) were added benzyl bromide (13 mg) and cesium carbonate (26 mg). The mixture was stirred overnight at r.t. The mixture was diluted with ethyl acetate and washed with water. The organic phase was dried (MgSO$_4$), filtered and concentrated under reduced pressure. The product was purified by chromatography (SiO$_2$, cyclohexane/ethyl acetate 1:0 to 1:1) to give N-benzyl-2-chloro-N-[2-(3-methanesulfonyl-phenyl)-thiazol-5-ylmethyl]-benzenesulfonamide as a colorless solid. MS: 534.8 ([M+H]$^+$)

Example 11

2-Chloro-N-isobutyl-N-[2-(3-methanesulfonyl-phenyl)-thiazol-5-ylmethyl]-benzenesulfonamide In analogy to example 10, step 3, 2-chloro-N-[2-(3-methanesulfonyl-phenyl)-thiazol-5-ylmethyl]-benzenesulfonamide (example 10, step 2) was reacted with 1-iodo-2-methylpropane and cesium carbonate in N,N-dimethylacetamide to give 2-chloro-N-isobutyl-N-[2-(3-methanesulfonyl-phenyl)-thiazol-5-ylmethyl]-benzenesulfonamide as a colorless solid. MS: 499.0 ([M+H]$^+$)

Example 12

N-Benzoyl-2-chloro-N-[2-(3-methanesulfonyl-phenyl)-thiazol-5-ylmethyl]-benzenesulfonamide In analogy to example 6, 2-chloro-N-[2-(3-methanesulfonyl-phenyl)-thiazol-5-ylmethyl]-benzenesulfonamide (example 10, step 2) was reacted with benzoyl chloride and N,N-diisopropyl ethyl amine in dichloromethane to give N-benzoyl-2-chloro-N-[2-(3-methanesulfonyl-phenyl)-thiazol-5-ylmethyl]-benzenesulfonamide as a colorless solid. MS: 548.7 ([M+H]$^+$)

Example 13

2-Chloro-N-isobutyl-N-[5-(3-methanesulfonyl-phenyl)-furan-2-ylmethyl]-benzenesulfonamide Step 1: To a stirred solution of 5-bromo-2-furaldehyde (500 mg) in methanol (5 mL) was added isobutylamine (209 mg). The mixture was stirred overnight at r.t. Sodium borohydride (162 mg) was added and the mixture was stirred for 2 h. The solvent was evaporated under reduced pressure. The residue was dissolved in ethyl acetate and washed with water. The organic phase was dried (MgSO$_4$), filtered and concentrated under reduced pressure to give the crude (5-bromo-furan-2-ylmethyl)-isobutyl-amine (686 mg) as a colorless oil which was used in the next step without further purification.

Step 2: To a stirred solution of the crude (5-bromo-furan-2-ylmethyl)-isobutyl-amine from step 1 (686 mg) in dichloromethane (8 mL) were added N,N-diisopropyl ethyl amine (686 mg) and 2-chlorobenzenesulfonylchloride (458 mg). The mixture was stirred for 18 h at r.t. Water was added and the mixture was extracted with dichloromethane. The organic phase was dried (MgSO$_4$), filtered and concentrated under reduced pressure. The product was purified by chromatography (SiO$_2$, cyclohexane/ethyl acetate 4:2) to give N-(5-bromo-furan-2-ylmethyl)-2-chloro-N-isobutyl-benzenesulfonamide (1.2 g) as a colorless oil.

Step 3: In analogy to example 1, step 3, N-(5-bromo-furan-2-ylmethyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-[5-(3-methanesulfonyl-phenyl)-furan-2-ylmethyl]-benzenesulfonamide as a light yellow oil. MS: 498.9 ([M+NH$_4$]$^+$)

Example 14

2-Chloro-N-isobutyl-N-[4-(3-methanesulfonyl-phenyl)-thiophen-2-ylmethyl]-benzenesulfonamide Step 1: In analogy to example 13, step 1, 4-bromothiophene-2-carboxaldehyde was reacted with isobutylamine and sodium borohydride in methanol to give (4-bromo-thiophen-2-ylmethyl)-isobutyl-amine as a colorless oil.

Step 2: In analogy to example 13, step 2, (4-bromo-thiophen-2-ylmethyl)-isobutyl-amine was reacted with 2-chlorobenzenesulfonylchloride in presence of N,N-diisopropyl ethyl amine in dichloromethane to give N-(4-bromo-thiophen-2-ylmethyl)-2-chloro-N-isobutyl-benzenesulfonamide as a colorless oil.

Step 3: In analogy to example 1, step 3, N-(4-bromo-thiophen-2-ylmethyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-[4-(3-methanesulfonyl-phenyl)-thiophen-2-ylmethyl]-benzenesulfonamide as a light yellow oil. MS: 514.9 ([M+NH$_4$]$^+$)

Example 15

N-Isobutyl-N-[5-(3-methanesulfonyl-phenyl)-thiophen-2-ylmethyl]-methanesulfonamide Step 1: In analogy to example 13, step 1, 5-bromothiophene-2-carboxaldehyde was reacted with isobutylamine and sodium borohydride in methanol to give (5-bromo-thiophen-2-ylmethyl)-isobutyl-amine as a colorless oil.

Step 2: In analogy to example 1, step 3, (5-bromo-thiophen-2-ylmethyl)-isobutyl-amine was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give isobutyl-[5-(3-methanesulfonyl-phenyl)-thiophen-2-ylmethyl]-amine as a light yellow oil. MS: 324.3 ([M+H]$^+$)

Step 3: In analogy to example 13, step 2, isobutyl-[5-(3-methanesulfonyl-phenyl)-thiophen-2-ylmethyl]-amine was reacted with methanesulfonyl chloride in presence of N,N-diisopropyl ethyl amine in dichloromethane to give N-isobutyl-N-[5-(3-methanesulfonyl-phenyl)-thiophen-2-ylmethyl]-methanesulfonamide as a colorless solid. MS: 419.3 ([M+NH$_4$]$^+$)

Example 16

Ethanesulfonic acid isobutyl-[5-(3-methanesulfonyl-phenyl)-thiophen-2-ylmethyl]-amide In analogy to example 13, step 2, isobutyl-[5-(3-methanesulfonyl-phenyl)-thiophen-2-ylmethyl]-amine (example 15, step 2) was reacted with ethanesulfonyl chloride and N,N-diisopropyl ethyl amine in dichloromethane to give ethanesulfonic acid isobutyl-[5-(3-methanesulfonyl-phenyl)-thiophen-2-ylmethyl]-amide as a light yellow oil. MS: 433.4 ($[M+NH_4]^+$)

Example 17

2-Fluoro-N-isobutyl-N-[5-(3-methanesulfonyl-phenyl)-thiophen-2-ylmethyl]-benzenesulfonamide In analogy to example 13, step 2, isobutyl-[5-(3-methanesulfonyl-phenyl)-thiophen-2-ylmethyl]-amine (example 15, step 2) was reacted with 2-fluorophenylsulfonyl chloride in presence of N,N-diisopropyl ethyl amine in dichloromethane to give 2-fluoro-N-isobutyl-N-[5-(3-methanesulfonyl-phenyl)-thiophen-2-ylmethyl]-benzenesulfonamide as a colorless oil. MS: 499.3 ($[M+NH_4]^+$)

Example 18

2,6-Dichloro-N-isobutyl-N-[5-(3-methanesulfonyl-phenyl)-thiophen-2-ylmethyl]-benzenesulfonamide In analogy to example 13, step 2, isobutyl-[5-(3-methanesulfonyl-phenyl)-thiophen-2-ylmethyl]-amine (example 15, step 2) was reacted with 2,6-dichlorophenylsulfonyl chloride in presence of N,N-diisopropyl ethyl amine in dichloromethane to give 2,6-dichloro-N-isobutyl-N-[5-(3-methanesulfonyl-phenyl)-thiophen-2-ylmethyl]-benzenesulfonamide as a colorless oil. MS: 549.3 ($[M+NH_4]^+$)

Example 19

2-{Isobutyl-[5-(3-methanesulfonyl-phenyl)-thiophen-2-ylmethyl]-sulfamoyl}-benzoic acid methyl ester In analogy to example 13, step 2, isobutyl-[5-(3-methanesulfonyl-phenyl)-thiophen-2-ylmethyl]-amine (example 15, step 2) was reacted with methyl-2-(chlorosulfonyl)-benzoate and N,N-diisopropyl ethyl amine in dichloromethane to give 2-{isobutyl-[5-(3-methanesulfonyl-phenyl)-thiophen-2-ylmethyl]-sulfamoyl}-benzoic acid methyl ester as a colorless oil. MS: 522.3 ($[M+H]^+$)

Example 20

Trifluoro-N-isobutyl-N-[5-(3-methanesulfonyl-phenyl)-thiophen-2-ylmethyl]-methanesulfonamide In analogy to example 13, step 2, isobutyl-[5-(3-methanesulfonyl-phenyl)-thiophen-2-ylmethyl]-amine (example 15, step 2) was reacted with trifluoromethanesulfonic anhydride and N,N-diisopropyl ethyl amine in dichloromethane to give trifluoro-N-isobutyl-N-[5-(3-methanesulfonyl-phenyl)-thiophen-2-ylmethyl]-methanesulfonamide as a light yellow oil. MS: 473.3 ($[M+NH_4]^+$)

Example 21

Thiophene-2-sulfonic acid isobutyl-[5-(3-methanesulfonyl-phenyl)-thiophen-2-ylmethyl]-amide In analogy to example 13, step 2, isobutyl-[5-(3-methanesulfonyl-phenyl)-thiophen-2-ylmethyl]-amine (example 15, step 2) was reacted with 2-thiophenesulfonyl chloride and N,N-diisopropyl ethyl amine in dichloromethane to give thiophene-2-sulfonic acid isobutyl-[5-(3-methanesulfonyl-phenyl)-thiophen-2-ylmethyl]-amide as a light yellow solid. MS: 487.0 ($[M+NH_4]^+$)

Example 22

3-Chloro-2-fluoro-N-isobutyl-N-[5-(3-methanesulfonyl-phenyl)-thiophen-2-ylmethyl]-benzenesulfonamide In analogy to example 13, step 2, isobutyl-[5-(3-methanesulfonyl-phenyl)-thiophen-2-ylmethyl]-amine (example 15, step 2) was reacted with 3-chloro-2-fluorophenylsulfonyl chloride and N,N-diisopropyl ethyl amine in dichloromethane to give 3-chloro-2-fluoro-N-isobutyl-N-[5-(3-methanesulfonyl-phenyl)-thiophen-2-ylmethyl]-benzenesulfonamide as a colorless oil. MS: 532.7 ($[M+NH_4]^+$)

Example 23

5-Chloro-N-isobutyl-N-[5-(3-methanesulfonyl-phenyl)-thiophen-2-ylmethyl]-2-methoxy-benzenesulfonamide In analogy to example 13, step 2, isobutyl-[5-(3-methanesulfonyl-phenyl)-thiophen-2-ylmethyl]-amine (example 15, step 2) was reacted with 5-chloro-2-methoxyphenylsulfonyl chloride and N,N-diisopropyl ethyl amine in dichloromethane to give 5-chloro-N-isobutyl-N-[5-(3-methanesulfonyl-phenyl)-thiophen-2-ylmethyl]-2-methoxy-benzenesulfonamide as a colorless oil. MS: 544.8 ($[M+NH_4]^+$)

Example 24

5-Fluoro-N-isobutyl-N-[5-(3-methanesulfonyl-phenyl)-thiophen-2-ylmethyl]-2-methyl-benzenesulfonamide In analogy to example 13, step 2, isobutyl-[5-(3-methanesulfonyl-phenyl)-thiophen-2-ylmethyl]-amine (example 15, step 2) was reacted with 5-fluoro-2-methylbenzenesulfonyl chloride and N,N-diisopropyl ethyl amine in dichloromethane to give 5-fluoro-N-isobutyl-N-[5-(3-methanesulfonyl-phenyl)-thiophen-2-ylmethyl]-2-methyl-benzenesulfonamide as a colorless oil. MS: 513.0 ($[M+NH_4]^+$)

Example 25

Butane-1-sulfonic acid isobutyl-[5-(3-methanesulfonyl-phenyl)-thiophen-2-ylmethyl]-amide To a stirred solution of isobutyl-[5-(3-methanesulfonyl-phenyl)-thiophen-2-ylmethyl]-amine (example 15, step 2, 56 mg) in dichloromethane (1 mL) were added dimethylketene methyltrimethylsilylacetal (60 mg) and 1-butanesulfonyl chloride (41 mg). The mixture was stirred for 2 days at r.t. The mixture was diluted with dichloromethane and washed with water. The organic phase was dried (MgSO$_4$), filtered and concentrated under reduced pressure. The product was purified by chromatography (SiO$_2$, cyclohexane/ethyl acetate 9:1 to 1:1) to give butane-1-sulfonic acid isobutyl-[5-(3-methanesulfonyl-phenyl)-thiophen-2-ylmethyl]-amide as a colorless solid. MS: 461.4 ([M+NH$_4$]$^+$)

Example 26

2-Cyano-N-isobutyl-N-[5-(3-methanesulfonyl-phenyl)-thiophen-2-ylmethyl]-benzenesulfonamide In analogy to example 13, step 2, isobutyl-[5-(3-methanesulfonyl-phenyl)-thiophen-2-ylmethyl]-amine (example 15, step 2) was reacted with 2-cyanobenzenesulfonyl chloride and N,N-diisopropyl ethyl amine in dichloromethane to give 2-cyano-N-isobutyl-N-[5-(3-methanesulfonyl-phenyl)-thiophen-2-ylmethyl]-benzenesulfonamide as a colorless solid. MS: 505.8 ([M+NH$_4$]$^+$)

Example 27

N-[5-(3-Methanesulfonyl-phenyl)-thiophen-2-ylmethyl]-N-methyl-2-trifluoromethyl-benzenesulfonamide Step 1: In analogy to example 1, step 3, N-(5-bromothiophen-2-ylmethyl)-2-trifluoromethyl-benzenesulfonamide (example 1, step 1) was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give N-[5-(3-methanesulfonyl-phenyl)-thiophen-2-ylmethyl]-2-trifluoromethyl-benzenesulfonamide as a light yellow solid. MS: 492.9 ([M+NH$_4$]$^+$)

Step 2: In analogy to example 10, step 3, N-[5-(3-methanesulfonyl-phenyl)-thiophen-2-ylmethyl]-2-trifluoromethyl-benzenesulfonamide (example 27, step 1) was reacted with iodomethane and cesium carbonate in N,N-dimethylacetamide to give N-[5-(3-methanesulfonyl-phenyl)-thiophen-2-ylmethyl]-N-methyl-2-trifluoromethyl-benzenesulfonamide as a light yellow semi-solid. MS: 506.9 ([M+H]$^+$)

Example 28

N-Ethyl-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with iodoethane and cesium carbonate in N,N-dimethylacetamide to give N-ethyl-N-[5-(3-methanesulfonyl-phenyl)-thiophen-2-ylmethyl]-2-trifluoromethyl-benzenesulfonamide as a light yellow oil. MS: 520.9 ([M+NH$_4$]$^+$)

Example 29

N-[5-(3-Methanesulfonyl-phenyl)-thiophen-2-ylmethyl]-N-propyl-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with iodopropane and cesium carbonate in N,N-dimethylacetamide to give N-[5-(3-methanesulfonyl-phenyl)-thiophen-2-ylmethyl]-N-propyl-2-trifluoromethyl-benzenesulfonamide as a light yellow oil. MS: 534.8 ([M+NH$_4$]$^+$)

Example 30

N-Isopropyl-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with isopropyl iodide and cesium carbonate in N,N-dimethylacetamide to give N-isopropyl-N-[5-(3-methanesulfonyl-phenyl)-thiophen-2-ylmethyl]-2-trifluoromethyl-benzenesulfonamide as a light yellow oil. MS: 534.8 ([M+NH$_4$]$^+$)

Example 31

N-Isobutyl-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with isobutyl iodide and cesium carbonate in N,N-dimethylacetamide to give N-isobutyl-N-[5-(3-methanesulfonyl-phenyl)-thiophen-2-ylmethyl]-2-trifluoromethyl-benzenesulfonamide as a colorless solid. MS: 548.8 ([M+NH$_4$]$^+$)

Example 32

N-Cyclopropylmethyl-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with (bromomethyl)-cyclopropane and cesium carbonate in N,N-dimethylacetamide to give N-cyclopropylmethyl-N-[5-(3-methanesulfonyl-phenyl)-thiophen-2-ylmethyl]-2-trifluoromethyl-benzenesulfonamide as a light yellow oil. MS: 546.8 ([M+NH$_4$]$^+$)

Example 33

N-(2-Fluoro-benzyl)-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with 2-fluorobenzyl bromide and cesium carbonate in N,N-dimethylacetamide to give N-(2-fluoro-benzyl)-N-[5-(3-methanesulfonyl-phenyl)-thiophen-2-ylmethyl]-2-trifluoromethyl-benzenesulfonamide as a light yellow oil. MS: 600.6 ([M+NH$_4$]$^+$)

Example 34

N-(3,5-Dimethyl-isoxazol-4-ylmethyl)-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with 4-(chloromethyl)-3,5-dimethylisoxazole, cesium carbonate and 10 mol-% tetrabutylammonium iodide as a catalyst in N,N-dimethylacetamide to give N-(3,5-dimethyl-isoxazol-4-ylmethyl)-N-[5-(3-methanesulfonyl-phenyl)-thiophen-2-ylmethyl]-2-trifluoromethyl-benzenesulfonamide as a colorless semi-solid. MS: 584.6 ([M+H]$^+$)

Example 35

N-[5-(3-Methanesulfonyl-phenyl)-thiophen-2-ylmethyl]-N-(2-methoxy-ethyl)-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with 2-bromoethyl methyl ether and cesium carbonate in N,N-dimethylacetamide to give N-[5-(3-methanesulfonyl-phenyl)-thiophen-2-ylmethyl]-N-(2-methoxy-ethyl)-2-trifluoromethyl-benzenesulfonamide as a light yellow oil. MS: 550.8 ([M+NH$_4$]$^+$)

Example 36

N-Cyclobutylmethyl-N-[5-(3-methanesulfonyl-phenyl)-thiophen-2-ylmethyl]-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with (bromomethyl)-cyclobutane and cesium carbonate in N,N-dimethylacetamide to give N-cyclobutylmethyl-N-[5-(3-methanesulfonyl-phenyl)-thiophen-2-ylmethyl]-2-trifluoromethyl-benzenesulfonamide as a light yellow semi-solid. MS: 560.7 ([M+NH$_4$]$^+$)

Example 37

[[5-(3-Methanesulfonyl-phenyl)-thiophen-2-ylmethyl]-(2-trifluoromethyl-benzenesulfonyl)-amino]-acetic acid tert-butyl ester In analogy to example 10, step 3, N-[5-(3-methanesulfonyl-phenyl)-thiophen-2-ylmethyl]-2-trifluoromethyl-benzenesulfonamide (example 27, step 1) was reacted with tert-butylchloroacetate and cesium carbonate in N,N-dimethylacetamide to give [[5-(3-methanesulfonyl-phenyl)-thiophen-2-ylmethyl]-(2-trifluoromethyl-benzenesulfonyl)-amino]-acetic acid tert-butyl ester as a light yellow oil. MS: 606.6 ([M+NH$_4$]$^+$)

Example 38

N,N-Diethyl-2-[[5-(3-methanesulfonyl-phenyl)-thiophen-2-ylmethyl]-(2-trifluoromethyl-benzenesulfonyl)-amino]-acetamide In analogy to example 10, step 3, N-[5-(3-methanesulfonyl-phenyl)-thiophen-2-ylmethyl]-2-trifluoromethyl-benzenesulfonamide (example 27, step 1) was reacted with N,N-diethylchloro acetamide and cesium carbonate in N,N-dimethylacetamide for 1 day at r.t., for 18 h at 50° C. and for 6 h at 100° C. to give N,N-diethyl-2-[[5-(3-methanesulfonyl-phenyl)-thiophen-2-ylmethyl]-(2-trifluoromethyl-benzenesulfonyl)-amino]-acetamide as a light yellow oil. MS: 588.8 ([M+NH$_4$]$^+$)

Example 39

N-[1,3]Dioxolan-2-ylmethyl-N-[5-(3-methanesulfonyl-phenyl)-thiophen-2-ylmethyl]-2-trifluoromethyl-benzenesulfonamide To a stirred solution of N-[5-(3-methanesulfonyl-phenyl)-thiophen-2-ylmethyl]-2-trifluoromethyl-benzenesulfonamide (example 27, step 1, 44 mg) in N,N-dimethylacetamide (0.8 mL) were added cesium carbonate (45 mg), 2-bromomethyl-1,3-dioxolane (23 mg) and tetrabutylammonium iodide (3 mg). The mixture was stirred for 3 days at r.t. More tetrabutylammonium iodide (3 mg) and 2-bromomethyl-1,3-dioxolane (23 mg) were added and the mixture was stirred for 18 h at r.t. and for 24 h at 50° C. 2-Bromomethyl-1,3-dioxolane (23 mg) was added and the mixture was stirred for 5 h at 100° C. The mixture was diluted with ethyl acetate and washed with water. The organic phase was dried (MgSO$_4$), filtered and concentrated under reduced pressure. The product was purified by chromatography (SiO$_2$, cyclohexane/ethyl acetate 9:1 to 1:1) to give N-[1,3]dioxolan-2-ylmethyl-N-[5-(3-methanesulfonyl-phenyl)-thiophen-2-ylmethyl]-2-trifluoromethyl-benzenesulfonamide (34 mg) as a light yellow oil. MS: 578.6 ([M+NH$_4$]$^+$)

Example 40

N-[5-(3-Methanesulfonyl-phenyl)-thiophen-2-ylmethyl]-N-(2-pyrrolidin-1-yl-ethyl)-2-trifluoromethyl-benzenesulfonamide In analogy to example 10, step 3, N-[5-(3-methanesulfonyl-phenyl)-thiophen-2-ylmethyl]-2-trifluoromethyl-benzenesulfonamide (example 27, step 1) was reacted with 1-(2-chloroethyl)pyrrolidine and cesium carbonate in N,N-dimethylacetamide for 3 days at r.t. to give N-[5-(3-methanesulfonyl-phenyl)-thiophen-2-ylmethyl]-N-(2-pyrrolidin-1-yl-ethyl)-2-trifluoromethyl-benzenesulfonamide as a light yellow oil. MS: 572.6 ([M+H]$^+$)

Example 41

N-[5-(3-Methanesulfonyl-phenyl)-thiophen-2-ylmethyl]-N-(tetrahydro-furan-2-ylmethyl)-2-trifluoromethyl-benzenesulfonamide To a stirred solution of N-[5-(3-methanesulfonyl-phenyl)-thiophen-2-ylmethyl]-2-trifluoromethyl-benzenesulfonamide (example 27, step 1, 52 mg) in N,N-dimethylacetamide (0.9 mL) were added cesium carbonate (54 mg), tetrahydrofurfuryl chloride (20 mg) and tetrabutylammonium iodide (4 mg). The mixture was stirred for 3 days at r.t. and for 1 day at 50° C. Tetrahydrofurfuryl chloride (20 mg) was added and the mixture was heated to 100° C. in the microwave oven for 10 min. The mixture was diluted with ethyl acetate and washed with water. The organic phase was dried (MgSO$_4$), filtered and concentrated under reduced pressure. The product was purified by chromatography (SiO$_2$, cyclohexane/ethyl acetate 95:5 to 1:1) to give N-[5-(3-methanesulfonyl-phenyl)-thiophen-2-ylmethyl]-N-(tetrahydro-furan-2-ylmethyl)-2- trifluoromethyl-benzenesulfonamide (37 mg) as a light yellow oil. MS: 576.7 ([M+NH$_4$]$^+$)

Example 42

2-Chloro-N-(3-fluoro-3'-methanesulfonyl-biphenyl-4-ylmethyl)-N-isobutyl-benzenesulfonamide Step 1: In analogy to example 1, step 1, isobutylamine was reacted with 2-chlorobenzenesulfonyl chloride and N,N-diisopropyl ethyl amine in dichloromethane to give 2-chloro-N-isobutyl-benzenesulfonamide as a colorless solid. MS: 248.1 ([M+H]$^+$)

Step 2: In analogy to example 10, step 3, 2-chloro-N-isobutyl-benzenesulfonamide was reacted with 4-bromo-2-fluorobenzyl bromide, cesium carbonate and 10 mol-% tetrabutylammonium iodide as a catalyst in N,N-dimethylacetamide to give N-(4-bromo-2-fluoro-benzyl)-2-chloro-N-isobutyl-benzenesulfonamide as a colorless oil. MS: 434.2 ([M+H]$^+$)

Step 3: In analogy to example 1, step 3, N-(4-bromo-2-fluoro-benzyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-(3-fluoro-3'-methanesulfonyl-biphenyl-4-ylmethyl)-N-isobutyl-benzenesulfonamide as a colorless solid. MS: 568.2 ([M+OAc]$^-$)

Example 43

2-Chloro-N-isobutyl-N-(3'-methanesulfonyl-biphenyl-3-ylmethyl)-benzenesulfonamide Step 1: In analogy to example 10, step 3, 2-chloro-N-isobutyl-benzenesulfonamide (example 42, step 1) was reacted with 3-bromobenzylbromide, cesium carbonate and 10 mol-% tetrabutylammonium iodide as a catalyst in N,N-dimethylacetamide to give N-(3-bromobenzyl)-2-chloro-N-isobutyl-benzenesulfonamide as a colorless oil. MS: 416.2 ([M+H]$^+$)

Step 2: In analogy to example 1, step 3, N-(3-bromo-benzyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-(3'-methanesulfonyl-biphenyl-3-ylmethyl)-benzenesulfonamide as a colorless solid. MS: 550.2 ([M+OAc]$^-$)

Example 44

2-Chloro-N-isobutyl-N-[5-(3-methanesulfonyl-phenyl)-pyridin-3-ylmethyl]-benzenesulfonamide Step 1: In analogy to example 10, step 3, 2-chloro-N-isobutyl-benzenesulfonamide (example 42, step 1) was reacted with 3-bromo-5-(chloromethyl)pyridine hydrochloride and cesium carbonate in N,N-dimethylacetamide to give N-(5-bromo-pyridin-3-ylmethyl)-2-chloro-N-isobutyl-benzenesulfonamide as a colorless oil. MS: 417.2 ([M+H]$^+$)

Step 2: In analogy to example 1, step 3, N-(5-bromo-pyridin-3-ylmethyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-[5-(3-methanesulfonyl-phenyl)-pyridin-3-ylmethyl]-benzenesulfonamide as a colorless solid. MS: 492.9 ([M+H]$^+$)

Example 45

2-Chloro-N-isobutyl-N-[5-(3-methanesulfonyl-phenyl)-pyridin-2-ylmethyl]-benzenesulfonamide Step 1: To a stirred solution of 2-chloro-N-isobutyl-benzenesulfonamide (example 42, step 1, 110 mg) in tetrahydrofuran (2.5 mL) were added (5-bromo-pyridin-2-yl)-methanol (CAS [88139-91-7], 92 mg), triphenylphosphine (129 mg) and diethyl azodicarboxylate (88 mg). The mixture was stirred for 48 h at r.t. The solvent was evaporated under reduced pressure and the product was purified by chromatography (SiO$_2$, cyclohexane/ethyl acetate 1:0 to 0:1) to give N-(5-bromo-pyridin-2-ylmethyl)-2-chloro-N-isobutyl-benzenesulfonamide (106 mg) as a colorless oil. MS: 417.2 ([M+H]$^+$)

Step 2: In analogy to example 1, step 3, N-(5-bromo-pyridin-2-ylmethyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-[5-(3-methanesulfonyl-phenyl)-pyridin-2-ylmethyl]-benzenesulfonamide as a colorless solid. MS: 493.0 ([M+H]$^+$)

Example 46

N-Benzyl-N-[5-(4-hydroxymethyl-3-methanesulfonyl-phenyl)-thiophen-2-ylmethyl]-2-trifluoromethyl-benzenesulfonamide A suspension of N-benzyl-N-(5-bromo-thiophen-2-ylmethyl)-2-trifluoromethyl-benzenesulfonamide (example 1, step 2, 170 mg), [2-methanesulfonyl-4-(4,4,5,5-tetramethyl-[1,3,2]dioxaborolan-2-yl)-phenyl]-methanol (CAS [918328-16-2], 90 mg), cesium fluoride (88 mg) and dichloro[1,1'-bis(diphenylphosphino)ferrocene]palladium dichloromethane adduct (12 mg) in a 1 M aqueous sodium carbonate solution (0.72 mL) and 1,2-dimethoxyethane (1.5 mL) was heated to 80° C. for 36 h. After cooling to r.t., the mixture was filtered. The filtrate was diluted with ethyl acetate and washed with water. The organic phase was dried (MgSO$_4$), filtered and concentrated under reduced pressure. The product was purified by chromatography (SiO$_2$, cyclohexane/ethyl acetate 1:0 to 0:1) to give N-benzyl-N-[5-(4-hydroxymethyl-3-methanesulfonyl-phenyl)-thiophen-2-ylmethyl]-2-trifluoromethyl-benzenesulfonamide (67 mg) as an off-white solid. MS: 612.6 ([M+NH$_4$]$^+$)

Example 47

2-Chloro-N-isobutyl-N-[6-(3-methanesulfonyl-phenyl)-pyridin-2-ylmethyl]-benzenesulfonamide Step 1: In analogy to example 45, step 1, 2-chloro-N-isobutyl-benzenesulfonamide (example 42, step 1) was reacted with 6-bromo-2-pyridinemethanol (CAS [33674-96-3]), triphenylphosphine and diethyl azodicarboxylate in tetrahydrofuran to give N-(6-bromo-pyridin-2-ylmethyl)-2-chloro-N-isobutyl-benzenesulfonamide as a colorless oil.

Step 2: In analogy to example 1, step 3, N-(6-bromo-pyridin-2-ylmethyl)-2-chloro-N-isobutyl-benzenesulfonamide was reacted with (3-methylsulfonylphenyl)-boronic

Example 48

2-Chloro-N-isobutyl-N-[2-(3-methanesulfonyl-phenyl)-pyridin-4-ylmethyl]-benzenesulfonamide Step 1: In analogy to example 45, step 1, 2-chloro-N-isobutyl-benzenesulfonamide (example 42, step 1) was reacted with (2-bromo-pyridin-4-yl)-methanol (CAS [118289-16-0]), triphenylphosphine and diethyl azodicarboxylate in tetrahydrofuran to give N-(2-bromo-pyridin-4-ylmethyl)-2-chloro-N-isobutyl-benzenesulfonamide as a colorless oil. MS: 417.2 ([M+H]$^+$)

Step 2: In analogy to example 1, step 3, N-(2-bromo-pyridin-4-ylmethyl)-2-chloro-N-isobutyl-benzenesulfonamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give 2-chloro-N-isobutyl-N-[2-(3-methanesulfonyl-phenyl)-pyridin-4-ylmethyl]-benzenesulfonamide as a colorless solid. MS: 492.9 ([M+H]$^+$)

Example 49

Propane-2-sulfonic acid (3'-methanesulfonyl-biphenyl-3-ylmethyl)-propyl-amide

Step 1: In analogy to example 1, step 1, 3-bromobenzylamine hydrochloride was reacted with isopropylsulfonyl chloride and triethylamine in dichloromethane to give propane-2-sulfonic acid 3-bromo-benzylamide as a colorless solid. MS: 290.0 ([M−H]$^-$)

Step 2: In analogy to example 1, step 3, propane-2-sulfonic acid 3-bromo-benzylamide was reacted with (3-methylsulfonylphenyl)-boronic acid, Na$_2$CO$_3$ and dichloro[1,1'-bis(diphenylphosphino)ferrocene]palladium dichloromethane adduct in dioxane/water to give propane-2-sulfonic acid (3'-methanesulfonyl-biphenyl-3-ylmethyl)-amide as an off-white solid.

Step 3: In analogy to example 10, step 3, propane-2-sulfonic acid (3'-methanesulfonyl-biphenyl-3-ylmethyl)-amide was reacted with 1-iodopropane and cesium carbonate in N,N-dimethylacetamide to give propane-2-sulfonic acid (3'-methanesulfonyl-biphenyl-3-ylmethyl)-propyl-amide as a colorless, waxy solid. MS: 427.2 ([M+NH$_4$]$^+$)

Example 50

Propane-2-sulfonic acid isobutyl-(3'-methanesulfonyl-biphenyl-3-ylmethyl)-amide

In analogy to example 10, step 3, propane-2-sulfonic acid (3'-methanesulfonyl-biphenyl-3-ylmethyl)-amide (example 49, step 2) was reacted with 1-iodo-2-methylpropane and cesium carbonate in N,N-dimethylacetamide to give propane-2-sulfonic acid isobutyl-(3'-methanesulfonyl-biphenyl-3-ylmethyl)-amide as an off-white solid. MS: 441.3 ([M+NH$_4$]$^+$)

Example 51

Propane-2-sulfonic acid cyclobutylmethyl-(3'-methanesulfonyl-biphenyl-3-ylmethyl)-amide In analogy to example 10, step 3, propane-2-sulfonic acid (3'-methanesulfonyl-biphenyl-3-ylmethyl)-amide (example 49, step 2) was reacted with cyclobutylmethyl bromide, tetrabutylammonium iodide and cesium carbonate in N,N-dimethylacetamide to give propane-2-sulfonic acid cyclobutylmethyl-(3'-methanesulfonyl-biphenyl-3-ylmethyl)-amide as a colorless semi-solid. MS: 436.3 ([M+H]$^+$)

Example 52

Propane-2-sulfonic acid (2-fluoro-benzyl)-(3'-methanesulfonyl-biphenyl-3-ylmethyl)-amide In analogy to example 10, step 3, propane-2-sulfonic acid (3'-methanesulfonyl-biphenyl-3-ylmethyl)-amide (example 49, step 2) was reacted with 2-fluorobenzyl bromide, tetrabutylammonium iodide and cesium carbonate in N,N-dimethylacetamide to give propane-2-sulfonic acid (2-fluoro-benzyl)-(3'-methanesulfonyl-biphenyl-3-ylmethyl)-amide as a colorless solid. MS: 476.4 ([M+H]$^+$)

Example 53

Propane-2-sulfonic acid (4-fluoro-benzyl)-(3'-methanesulfonyl-biphenyl-3-ylmethyl)-amide In analogy to example 10, step 3, propane-2-sulfonic acid (3'-methanesulfonyl-biphenyl-3-ylmethyl)-amide (example 49, step 2) was reacted with 4-fluorobenzyl bromide, tetrabutylammonium iodide and cesium carbonate in N,N-dimethylacetamide to give propane-2-sulfonic acid (4-fluoro-benzyl)-(3'-methanesulfonyl-biphenyl-3-ylmethyl)-amide as a colorless solid. MS: 493.3 ([M+NH$_4$]$^+$)

Example 54

2-Chloro-N-isobutyl-N-[4-(3-aminosulfonyl-phenyl)-thiophen-2-ylmethyl]-benzenesulfonamide In analogy to example 1, step 3, N-(4-bromo-thiophen-2-ylmethyl)-2-chloro-N-isobutyl-benzenesulfonamide (example 14, step 2) was reacted with (3-aminosulfonyl)-benzeneboronic acid, Na$_2$CO$_3$ and dichloro[1,1'-bis(diphenylphosphino)ferrocene]palladium dichloromethane adduct in dioxane/water to give 2-chloro-N-isobutyl-N-[4-(3-aminosulfonyl-phenyl)-thiophen-2-ylmethyl]-benzenesulfonamide as an off-white solid. MS: 497.1 ([M−H]$^-$)

Example 55

2-Chloro-N-isobutyl-N-[4-(5-methanesulfonyl-pyridin-3-yl)-thiophen-2-ylmethyl]-benzenesulfonamide In analogy to example 1, step 3, N-(4-bromo-thiophen-2-ylmethyl)-2-chloro-N-isobutyl-benzenesulfonamide (example 14, step 2) was reacted with 5-(methylsulfonyl)-3-pyridineboronic acid, Na$_2$CO$_3$ and dichloro[1,1'-bis(diphenylphosphino)ferrocene]palladium dichloromethane adduct in dioxane/water to give 2-chloro-N-isobutyl-N-[4-(5-methanesulfonyl-pyridin-3-yl)-thiophen-2-ylmethyl]-benzenesulfonamide as an off-white solid. MS: 557.1 ([M+OAc]$^-$)

Example 56

2-Chloro-N-isobutyl-N-[4-(3-tert-butylaminosulfonyl-phenyl)-thiophen-2-ylmethyl]-benzenesulfonamide In analogy to example 1, step 3, N-(4-bromo-thiophen-2-ylmethyl)-2-chloro-N-isobutyl-benzenesulfonamide (example 14, step 2) was reacted with 3-tert-butylsulfamoyl-benzeneboronic acid (CAS [221290-14-8]), $Na_2CO_3$ and dichloro[1,1'-bis(diphenylphosphino)ferrocene]palladium dichloromethane adduct in dioxane/water to give 2-chloro-N-isobutyl-N-[4-(3-tert-butylaminosulfonyl-phenyl)-thiophen-2-ylmethyl]-benzenesulfonamide as an off-white solid. MS: 553.6 ($[M-H]^-$)

Example 57

N-Isobutyl-N-[5-(3-methanesulfonyl-phenyl)-thiophen-2-ylmethyl]-C-phenyl-methanesulfonamide In analogy to example 13, step 2, isobutyl-[5-(3-methanesulfonyl-phenyl)-thiophen-2-ylmethyl]-amine (example 15, step 2) was reacted with alpha-toluenesulfonyl chloride and N,N-diisopropyl ethyl amine in dichloromethane to give N-isobutyl-N-[5-(3-methanesulfonyl-phenyl)-thiophen-2-ylmethyl]-C-phenyl-methanesulfonamide as an off-white solid. MS: 495.2 ($[M+NH_4]^+$)

Example 58

C-Cyclohexyl-N-isobutyl-N-[5-(3-methanesulfonyl-phenyl)-thiophen-2-ylmethyl]-methanesulfonamide In analogy to example 25, isobutyl-[5-(3-methanesulfonyl-phenyl)-thiophen-2-ylmethyl]-amine (example 15, step 2) was reacted with cyclohexyl-methane-sulfonylchloride and dimethylketene-methyltrimethylsilylacetal in dichloromethane to give C-cyclohexyl-N-isobutyl-N-[5-(3-methanesulfonyl-phenyl)-thiophen-2-ylmethyl]-methanesulfonamide as an off-white solid. MS: 500.9 ($[M+NH_4]^+$)

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titan dioxide | 0.8 mg | 1.6 mg |

The active ingredient is sieved and mixed with microcrystalline cellulose and the mixture is granulated with a solution of polyvinylpyrrolidon in water. The granulate is mixed with sodium starch glycolate and magesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Polyethylene Glycol 400 | 150.0 mg |
| Acetic Acid | q.s. ad pH 5.0 |
| Water for injection solutions | ad 1.0 ml |

The active ingredient is dissolved in a mixture of Polyethylene Glycol 400 and water for injection (part). The pH is adjusted to 5.0 by Acetic Acid. The volume is adjusted to 1.0 ml by addition of the residual amount of water. The solution is filtered, filled into vials using an appropriate overage and sterilized.

Example D

Soft gelatin capsules containing the following ingredients can be manufactured in a conventional manner:

| Capsule contents | |
|---|---|
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |
| Titan dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcristalline cellulose (AVICEL PH 102) | 1400.0 mg |
| Sodium carboxymethyl cellulose | 14.0 mg |
| Polyvinylpyrrolidon K 30 | 10.0 mg |
| Magnesiumstearate | 10.0 mg |
| Flavoring additives | 1.0 mg |

The active ingredient is mixed with lactose, microcristalline cellulose and sodium carboxymethyl cellulose and granulated with a mixture of polyvinylpyrrolidon in water. The granulate is mixed with magnesiumstearate and the flavoring additives and filled into sachets.

The invention claimed is:

1. A compound of formula (I)

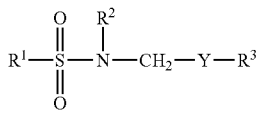

wherein
Y is arylene or heteroarylene, which arylene or heteroarylene can optionally be substituted with 1 to 4 substituents independently selected from the group consisting of halogen, lower-alkyl, lower-alkoxy, fluoro-lower-alkyl and fluoro-lower-alkoxy;
$R^1$ is lower-alkyl, fluoro-lower-alkyl, aryl, aryl-lower-alkyl, heteroaryl, heteroaryl-lower-alkyl, cycloalkyl or cycloalkyl-lower-alkyl, wherein an aryl, heteroaryl or cycloalkyl can optionally be substituted with 1 to 4 substituents independently selected from the group consisting of halogen, CN, lower-alkyl, lower-alkoxy, fluoro-lower-alkyl, fluoro-lower-alkoxy, lower-alkoxy-carbonyl and phenyl;
$R^2$ is lower-alkyl, lower-alkoxy-lower-alkyl, lower-alkoxy-carbonyl-lower-alkyl, amino-carbonyl-lower-alkyl, cycloalkyl, cycloalkyl-lower-alkyl, aryl-lower-alkyl, aryl-C(O), heteroaryl-lower-alkyl, heteroaryl-C(O) or heterocyclyl-lower-alkyl, wherein a cycloalkyl, aryl, heteroaryl or heterocyclyl can optionally be substituted with 1 to 4 substituents independently selected from the group consisting of halogen, lower-alkyl, CN, fluoro-lower-alkyl, lower-alkoxy, fluoro-lower-alkoxy and lower-alkoxy-carbonyl;
$R^3$ is aryl or heteroaryl, which aryl or heteroaryl is substituted with $R^4SO_2$—, $N(R^5R^6)SO_2$—, $R^4SO_2NR^7$— or $N(R^5R^6)SO_2NR^7$—, and which aryl or heteroaryl can optionally be substituted with 1 to 3 additional substituents independently selected from the group consisting of hydroxy-lower-alkyl, halogen, CN, lower-alkyl, fluoro-lower-alkyl, lower-alkoxy, fluoro-lower-alkoxy and lower-alkoxy-carbonyl;
$R^4$ is lower-alkyl;
$R^5$, $R^6$ and $R^7$ independently from each other are hydrogen or lower-alkyl;

and pharmaceutically acceptable salts and esters thereof; with the proviso that the compound is not N-[[3'-[(methylsulfonyl)amino][1,1'-biphenyl]-3-yl]methyl]-N-(3-pyridinylmethyl)-ethanesulfonamide.

2. The compound of claim 1 wherein Y is phenylene or a heteroarylene selected from the group consisting of thiophenylene, oxadiazolylene, thiazolylene, furanylene and pyridinylene, which phenylene or heteroarylene is optionally substituted with 1 to 2 halogen.

3. The compound of claim 2 wherein Y is phenylene, thiophenylene or pyridinylene, which phenylene is optionally substituted with halogen.

4. The compound of claim 3 wherein Y is

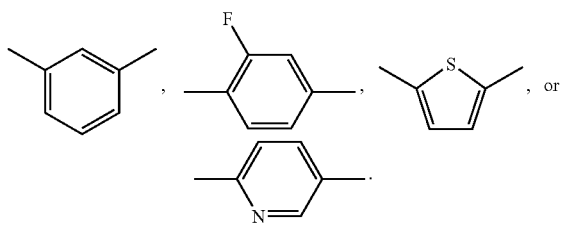

5. The compound of claim 1 wherein $R^1$ is lower-alkyl, fluoro-lower-alkyl, aryl, aryl-lower-alkyl, heteroaryl or cycloalkyl-lower-alkyl, wherein an aryl, heteroaryl or cycloalkyl can optionally be substituted with 1 to 3 substituents independently selected from the group consisting of halogen, CN, lower-alkyl, lower-alkoxy, fluoro-lower-alkyl and lower-alkoxy-carbonyl.

6. The compound of claim 5 wherein $R^1$ is lower-alkyl, fluoro-lower-alkyl or phenyl, which phenyl is optionally substituted with halogen, CN or fluoro-lower-alkyl.

7. The compound of claim 6 wherein $R^1$ is isopropyl, trifluoromethyl, 2-chloro-phenyl, 2-fluoro-phenyl, 2-cyano-phenyl or 2-trifluoromethyl-phenyl.

8. The compound of claim 1 wherein $R^2$ is lower-alkyl, lower-alkoxy-lower-alkyl, lower-alkoxy-carbonyl-lower-alkyl, amino-carbonyl-lower-alkyl, cycloalkyl-lower-alkyl, aryl-lower-alkyl, aryl-C(O), heteroaryl-lower-alkyl or heterocyclyl-lower-alkyl, wherein a cycloalkyl, aryl, heteroaryl or heterocyclyl can optionally be substituted with 1 to 3 substituents independently selected from the group consisting of halogen and lower-alkyl.

9. The compound of claim 8 wherein $R^2$ is lower-alkyl, cycloalkyl-lower-alkyl or aryl-lower-alkyl, wherein aryl-lower-alkyl can optionally be substituted with halogen.

10. The compound of claim 9 wherein $R^2$ is isopropyl, isobutyl, cyclopropylmethyl or 2-fluoro-benzyl.

11. The compound of claim 1 wherein $R^3$ is aryl or heteroaryl, which aryl or heteroaryl is substituted with $R^4SO_2$—, $N(R^5R^6)SO_2$— or $R^4SO_2NR^7$—, and which aryl or heteroaryl can optionally be substituted with 1 to 2 additional substituents independently selected from hydroxy-lower-alkyl, wherein $R^4$, $R^5$, $R^6$ and $R^7$ are as defined in claim 1.

12. The compound of claim 11 wherein $R^3$ is phenyl which is substituted with $R^4SO_2$—, wherein $R^4$ is as defined in claim 1.

13. The compound of claim 12 wherein $R^3$ is 3-methansulfonyl-phenyl.

14. The compound of claim 1 wherein $R^4$ is methyl.

15. The compound of claim 1 wherein $R^5$ is hydrogen.

16. The compound of claim 1 wherein $R^6$, is hydrogen or tert-butyl.

17. The compound of claim 1 wherein $R^7$ is hydrogen.

18. The compound of claim 1 selected from the group consisting of

N-Benzyl-N-[5-(3-methanesulfonyl-phenyl)-thiophen-2-ylmethyl]-2-trifluoromethyl-benzenesulfonamide, N-Benzyl-N-[5-(3-methanesulfonylamino-phenyl)-thiophen-2-ylmethyl]-2-trifluoromethyl-benzenesulfonamide, N-Benzyl-N-[5-(3-methanesulfonyl-phenyl)-[1,3,4]oxadiazol-2-ylmethyl]-2-trifluoromethyl-benzenesulfonamide, N-Benzyl-2-chloro-N-[5-(3-methanesulfonyl-phenyl)-thiophen-2-ylmethyl]-benzenesulfonamide, 2-Chloro-N-isobutyl-N-[5-(3-methanesulfonyl-phenyl)-thiophen-2-ylmethyl]-benzenesulfonamide, N-Benzoyl-2-chloro-N-[5-(3-methanesulfonyl-phenyl)-thiophen-2-ylmethyl]-benzenesulfonamide, N-Benzyl-3-chloro-N-[5-(3-methanesulfonyl-phenyl)-thiophen-2-ylmethyl]-benzenesulfonamide, 3-Chloro-N-isobutyl-N-[5-(3-methanesulfonyl-phenyl)-thiophen-2-ylmethyl]-benzenesulfonamide, N-Benzoyl-3-chloro-N-[5-(3-methanesulfonyl-phenyl)-thiophen-2-ylmethyl]-benzenesulfonamide, N-Benzyl-2-chloro-N-[2-(3-methanesulfonyl-phenyl)-thiazol-5-ylmethyl]-benzenesulfonamide, 2-Chloro-N-isobutyl-N-[2-(3-methanesulfonyl-phenyl)-thiazol-5-ylmethyl]-benzenesulfonamide, N-Benzoyl-2-chloro-N-[2-(3-methanesulfonyl-phenyl)-thiazol-5-ylmethyl]-benzenesulfonamide, 2-Chloro-N-isobutyl-N-[5-(3-methanesulfonyl-phenyl)-furan-2-ylmethyl]-benzenesulfonamide, 2-Chloro-N-isobutyl-N-[4-(3-methanesulfonyl-phenyl)-thiophen-2-ylmethyl]-benzenesulfonamide, N-Isobutyl-N-[5-(3-methanesulfonyl-phenyl)-thiophen-2-ylmethyl]-methanesulfonamide, Ethanesulfonic acid isobutyl-[5-(3-methanesulfonyl-phenyl)-thiophen-2-ylmethyl]-amide, 2-Fluoro-N-isobutyl-N-[5-(3-methanesulfonyl-phenyl)-thiophen-2-ylmethyl]-benzenesulfonamide, 2,6-Dichloro-N-isobutyl-N-[5-(3-methanesulfonyl-phenyl)-thiophen-2-ylmethyl]-benzenesulfonamide, 2-{Isobutyl-[5-(3-methanesulfonyl-phenyl)-thiophen-2-ylmethyl]-sulfamoyl}-benzoic acid methyl ester, Trifluoro-N-isobutyl-N-[5-(3-methanesulfonyl-phenyl)-thiophen-2-ylmethyl]-methanesulfonamide, Thiophene-2-sulfonic acid isobutyl-[5-(3-methanesulfonyl-phenyl)-thiophen-2-ylmethyl]-amide, 3-Chloro-2-fluoro-N-isobutyl-N-[5-(3-methanesulfonyl-phenyl)-thiophen-2-ylmethyl]-benzenesulfonamide, 5-Chloro-N-isobutyl-N-[5-(3-methanesulfonyl-phenyl)-thiophen-2-ylmethyl]-2-methoxy-benzenesulfonamide, 5-Fluoro-N-isobutyl-N-[5-(3-methanesulfonyl-phenyl)-thiophen-2-ylmethyl]-2-methyl-benzenesulfonamide, Butane-1-sulfonic acid isobutyl-[5-(3-methanesulfonyl-phenyl)-thiophen-2-ylmethyl]-amide, 2-Cyano-N-isobutyl-N-[5-(3-methanesulfonyl-phenyl)-thiophen-2-ylmethyl]-benzenesulfonamide, N-[5-(3-Methanesulfonyl-phenyl)-thiophen-2-ylmethyl]-N-methyl-2-trifluoromethyl-benzenesulfonamide, N-Ethyl-N-[5-(3-methanesulfonyl-phenyl)-thiophen-2-ylmethyl]-2-trifluoromethyl-benzenesulfonamide, N-[5-(3-Methanesulfonyl-phenyl)-thiophen-2-ylmethyl]-N-propyl-2-trifluoromethyl-benzenesulfonamide, N-Isopropyl-N-[5-(3-methanesulfonyl-phenyl)-thiophen-2-ylmethyl]-2-trifluoromethyl-benzenesulfonamide, N-Isobutyl-N-[5-(3-methanesulfonyl-phenyl)-thiophen-2-ylmethyl]-2-trifluoromethyl-benzenesulfonamide, N-Cyclopropylmethyl-N-[5-(3-methanesulfonyl-phenyl)-thiophen-2-ylmethyl]-2-trifluoromethyl-benzenesulfonamide, N-(2-Fluoro-benzyl)-N-[5-(3-methanesulfonyl-phenyl)-thiophen-2-ylmethyl]-2-trifluoromethyl-benzenesulfonamide, N-(3,5-Dimethyl-isoxazol-4-ylmethyl)-N-[5-(3-methanesulfonyl-phenyl)-thiophen-2-ylmethyl]-2-trifluoromethyl-benzenesulfonamide, N-[5-(3-Methanesulfonyl-phenyl)-thiophen-2-ylmethyl]-N-(2-methoxy-ethyl)-2-trifluoromethyl-benzenesulfonamide, N-Cyclobutylmethyl-N-[5-(3-methanesulfonyl-phenyl)-thiophen-2-ylmethyl]-2-trifluoromethyl-benzenesulfonamide,

[[5-(3-Methanesulfonyl-phenyl)-thiophen-2-ylmethyl]-(2-trifluoromethyl-benzenesulfonyl)-amino]-acetic acid tert-butyl ester, N,N-Diethyl-2-[[5-(3-methanesulfonyl-phenyl)-thiophen-2-ylmethyl]-(2-trifluoromethyl-benzenesulfonyl)-amino]-acetamide, N-[1,3]Dioxolan-2-ylmethyl-N-[5-(3-methanesulfonyl-phenyl)-thiophen-2-ylmethyl]-2-trifluoromethyl-benzenesulfonamide, N-[5-(3-Methanesulfonyl-phenyl)-thiophen-2-ylmethyl]-N-(2-pyrrolidin-1-yl-ethyl)-2-trifluoromethyl-benzenesulfonamide, N-[5-(3-Methanesulfonyl-phenyl)-thiophen-2-ylmethyl]-N-(tetrahydro-furan-2-ylmethyl)-2-trifluoromethyl-benzenesulfonamide, 2-Chloro-N-(3-fluoro-3'-methanesulfonyl-biphenyl-4-ylmethyl)-N-isobutyl-benzenesulfonamide, 2-Chloro-N-isobutyl-N-(3'-methanesulfonyl-biphenyl-3-ylmethyl)-benzenesulfonamide, 2-Chloro-N-isobutyl-N-[5-(3-methanesulfonyl-phenyl)-pyridin-3-ylmethyl]-benzenesulfonamide, 2-Chloro-N-isobutyl-N-[5-(3-methanesulfonyl-phenyl)-pyridin-2-ylmethyl]-benzenesulfonamide, N-Benzyl-N-[5-(4-hydroxymethyl-3-methanesulfonyl-phenyl)-thiophen-2-ylmethyl]-2-trifluoromethyl-benzenesulfonamide, 2-Chloro-N-isobutyl-N-[6-(3-methanesulfonyl-phenyl)-pyridin-2-ylmethyl]-benzenesulfonamide, 2-Chloro-N-isobutyl-N-[2-(3-methanesulfonyl-phenyl)-pyridin-4-ylmethyl]-benzenesulfonamide, Propane-2-sulfonic acid (3'-methanesulfonyl-biphenyl-3-ylmethyl)-propyl-amide, Propane-2-sulfonic acid isobutyl-(3'-methanesulfonyl-biphenyl-3-ylmethyl)-amide, Propane-2-sulfonic acid cyclobutylmethyl-(3'-methanesulfonyl-biphenyl-3-ylmethyl)-amide, Propane-2-sulfonic acid (2-fluoro-benzyl)-(3'-methanesulfonyl-biphenyl-3-ylmethyl)-amide, Propane-2-sulfonic acid (4-fluoro-benzyl)-(3'-methanesulfonyl-biphenyl-3-ylmethyl)-amide, 2-Chloro-N-isobutyl-N-[4-(3-aminosulfonyl-phenyl)-thiophen-2-ylmethyl]-benzenesulfonamide, 2-Chloro-N-isobutyl-N-[4-(5-methanesulfonyl-pyridin-3-yl)-thiophen-2-ylmethyl]-benzenesulfonamide, 2-Chloro-N-isobutyl-N-[4-(3-tert-butylaminosulfonyl-phenyl)-thiophen-2-ylmethyl]-benzenesulfonamide, N-Isobutyl-N-[5-(3-methanesulfonyl-phenyl)-thiophen-2-ylmethyl]-C-phenyl-methanesulfonamide, and C-Cyclohexyl-N-isobutyl-N-[5-(3-methanesulfonyl-phenyl)-thiophen-2-ylmethyl]-methanesulfonamide, and pharmaceutically acceptable salts and esters thereof.

19. The compound of claim 18 selected from the group consisting of

2-Fluoro-N-isobutyl-N-[5-(3-methanesulfonyl-phenyl)-thiophen-2-ylmethyl]-benzenesulfonamide, Trifluoro-N-isobutyl-N-[5-(3-methanesulfonyl-phenyl)-thiophen-2-ylmethyl]-methanesulfonamide, 2-Cyano-N-isobutyl-N-[5-(3-methanesulfonyl-phenyl)-thiophen-2-ylmethyl]-benzenesulfonamide, N-Isopropyl-N-[5-(3-methanesulfonyl-phenyl)-thiophen-2-ylmethyl]-2-trifluoromethyl-benzenesulfonamide, N-Cyclopropylmethyl-N-[5-(3-methanesulfonyl-phenyl)-thiophen-2-ylmethyl]-2-trifluoromethyl-benzenesulfonamide, 2-Chloro-N-(3-fluoro-3'-methanesulfonyl-biphenyl-4-ylmethyl)-N-isobutyl-benzenesulfonamide, 2-Chloro-N-isobutyl-N-[5-(3-methanesulfonyl-phenyl)-pyridin-2-ylmethyl]-benzenesulfonamide, and Propane-2-sulfonic acid (2-fluoro-benzyl)-(3'-methanesulfonyl-biphenyl-3-ylmethyl)-amide, and pharmaceutically acceptable salts and esters thereof.

20. A process for the manufacture of compounds of formula (I) as defined in claim 1 comprising a) reacting a compound of formula (II)

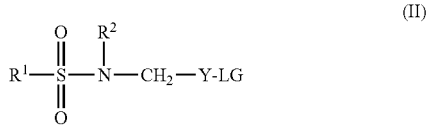

(II)

with a compound of formula $R^3$-M, or b) reacting a compound of formula (III)

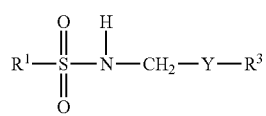

(III)

with a compound $R^2X$, or c) reacting a compound of formula (IV)

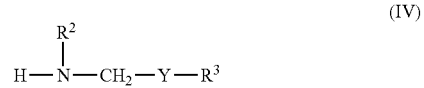

(IV)

with a compound $R^1SO_2Cl$, wherein $R^1$, $R^2$, $R^3$ and Y are as defined in any of claim 1; LG is Cl, Br, I, OMs, OTs or OTf; M is boronic acid or boronic acid ester; X is Cl, Br, I, OMs, OTs, OTf or OH.

21. The compound of claim 1 when manufactured by the process of claim 20.

22. A pharmaceutical composition comprising a therapeutically effective amount of the compound of claim 1 and a pharmaceutically acceptable carrier and/or adjuvant.

23. A method for the therapeutic treatment of diseases which are modulated by LXR alpha and/or LXR beta agonists, particularly for the therapeutic treatment of increased lipid levels, increased cholesterol levels, low HDL-cholesterol, high LDL-cholesterol, atherosclerotic diseases, diabetes, non-insulin dependent diabetes mellitus, metabolic syndrome, dyslipidemia, sepsis, inflammatory diseases, infectious diseases, skin diseases, colitis, pancreatitis, cholestasis of the liver, fibrosis of the liver, psoriasis, Alzheimer's disease, impaired/improvable cognitive function, HIV, cancer, age related forms of macular degeneration, inherited forms of macular degeneration and/or Stargadt's disease, which method comprises administering a compound of claim 1 to a human being or animal.

* * * * *

UNITED STATES PATENT AND TRADEMARK OFFICE
CERTIFICATE OF CORRECTION

| | | |
|---|---|---|
| PATENT NO. | : 8,039,493 B2 | Page 1 of 1 |
| APPLICATION NO. | : 12/211835 | |
| DATED | : October 18, 2011 | |
| INVENTOR(S) | : Henrietta Dehmlow et al. | |

It is certified that error appears in the above-identified patent and that said Letters Patent is hereby corrected as shown below:

On the Title Page: Insert

Item -- (30) Foreign Applications Priority Data
September 27, 2007 (EP) ...............07117437.9 --

Signed and Sealed this
Seventh Day of August, 2012

David J. Kappos
*Director of the United States Patent and Trademark Office*